(12) United States Patent
Lee et al.

(10) Patent No.: US 11,590,352 B2
(45) Date of Patent: Feb. 28, 2023

(54) RAMPED THERAPEUTIC SIGNALS FOR MODULATING INHIBITORY INTERNEURONS, AND ASSOCIATED SYSTEMS AND METHODS

(71) Applicant: Nevro Corp., Redwood City, CA (US)

(72) Inventors: Dongchul Lee, Agua Dulce, CA (US); Kerry Bradley, Glendale, CA (US); Kwan Yeop Lee, Mississauga (CA)

(73) Assignee: Nevro Corp., Redwood City, CA (US)

( * ) Notice: Subject to any disclaimer, the term of this patent is extended or adjusted under 35 U.S.C. 154(b) by 113 days.

(21) Appl. No.: 16/776,199

(22) Filed: Jan. 29, 2020

(65) Prior Publication Data

US 2020/0269051 A1 Aug. 27, 2020

Related U.S. Application Data

(60) Provisional application No. 62/798,334, filed on Jan. 29, 2019.

(51) Int. Cl.
*A61N 1/36* (2006.01)

(52) U.S. Cl.
CPC ..... *A61N 1/36071* (2013.01); *A61N 1/36192* (2013.01); *A61N 1/36196* (2013.01)

(58) Field of Classification Search
CPC ............ A61N 1/36071; A61N 1/36196; A61N 1/36192
See application file for complete search history.

(56) References Cited

U.S. PATENT DOCUMENTS

| | | | |
|---|---|---|---|
| 1,597,061 A | 8/1926 | Cultra | |
| 2,622,601 A | 12/1952 | Nemec | |
| 3,195,540 A | 7/1965 | Waller | |
| 3,279,468 A | 10/1966 | Vine | |
| 3,449,768 A | 6/1969 | Doyle | |
| 3,646,940 A | 3/1972 | Timm et al. | |
| 3,724,467 A | 4/1973 | Avery et al. | |
| 3,727,616 A | 4/1973 | Lenzkes | |

(Continued)

FOREIGN PATENT DOCUMENTS

| | | |
|---|---|---|
| CN | 101175530 | 5/2008 |
| DE | 10318071 A1 | 11/2004 |

(Continued)

OTHER PUBLICATIONS

U.S. Appl. No. 15/606,869, filed May 26, 2017, Lee.

(Continued)

*Primary Examiner* — Paula J Stice
(74) *Attorney, Agent, or Firm* — Perkins Coie LLP

(57) ABSTRACT

Systems and methods for treating a patient's pain using ramped therapeutic signals for modulating inhibitory interneurons, and associated systems and methods are disclosed. A representative method for treating a patient includes positioning an implantable signal delivery device proximate to a target location at or near the patient's spinal cord, and delivering an electrical therapy signal to the target location via the implantable signal delivery device, wherein the electrical therapy signal has a frequency in a frequency range of from about 1 kHz to about 100 kHz, and wherein the frequency is increased or decreased from a first value to a second value during delivery.

25 Claims, 12 Drawing Sheets

(56) References Cited

U.S. PATENT DOCUMENTS

| | | |
|---|---|---|
| 3,774,618 A | 11/1973 | Avery |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,096,866 A | 6/1978 | Fischell |
| 4,148,321 A | 4/1979 | Wyss et al. |
| 4,155,366 A | 5/1979 | Di Mucci |
| 4,289,136 A | 9/1981 | Rienzo, Sr. |
| 4,315,503 A | 2/1982 | Ryaby et al. |
| 4,379,462 A | 4/1983 | Borkan et al. |
| 4,414,986 A | 11/1983 | Dickhudt et al. |
| 4,459,989 A | 7/1984 | Borkan |
| 4,535,777 A | 8/1985 | Castel |
| 4,541,432 A | 9/1985 | Molina-Negro et al. |
| 4,550,733 A | 11/1985 | Liss et al. |
| 4,607,639 A | 8/1986 | Tanagho |
| 4,608,985 A | 9/1986 | Crish et al. |
| 4,612,934 A | 9/1986 | Borkan et al. |
| 4,649,935 A | 3/1987 | Charmillot et al. |
| 4,702,254 A | 10/1987 | Zabara |
| 4,735,204 A | 4/1988 | Sussman et al. |
| 4,739,764 A | 4/1988 | Lue et al. |
| 4,764,132 A | 8/1988 | Stutz, Jr. |
| 4,784,142 A | 11/1988 | Liss et al. |
| 4,793,353 A | 12/1988 | Borkan et al. |
| 4,841,973 A | 6/1989 | Stecker |
| RE33,420 E | 11/1990 | Sussman et al. |
| 4,989,605 A | 2/1991 | Rossen |
| 5,002,053 A | 3/1991 | Garcia-Rill |
| 5,042,486 A | 8/1991 | Pfeiler et al. |
| 5,052,375 A | 10/1991 | Stark et al. |
| 5,078,140 A | 1/1992 | Kwoh |
| 5,188,104 A | 2/1993 | Wernicke et al. |
| 5,211,165 A | 5/1993 | Dumoulin et al. |
| 5,257,636 A | 11/1993 | White |
| 5,284,153 A | 2/1994 | Raymond et al. |
| 5,306,291 A | 4/1994 | Kroll et al. |
| 5,325,873 A | 7/1994 | Hirschi et al. |
| 5,330,515 A | 7/1994 | Rutecki et al. |
| 5,335,657 A | 8/1994 | Terry, Jr. et al. |
| 5,354,320 A | 10/1994 | Schaldach et al. |
| 5,375,596 A | 12/1994 | Twiss et al. |
| 5,417,719 A | 5/1995 | Hull |
| 5,425,367 A | 6/1995 | Shapiro et al. |
| 5,501,703 A | 3/1996 | Holsheimer et al. |
| 5,514,175 A | 5/1996 | Kim et al. |
| 5,531,774 A | 7/1996 | Schulman et al. |
| 5,540,730 A | 7/1996 | Terry, Jr. et al. |
| 5,540,734 A | 7/1996 | Zabara |
| 5,562,717 A | 10/1996 | Tippey et al. |
| 5,573,552 A | 11/1996 | Hansjurgens et al. |
| 5,643,330 A | 7/1997 | Holsheimer et al. |
| 5,702,428 A | 12/1997 | Tippey et al. |
| 5,707,396 A | 1/1998 | Benabid |
| 5,716,377 A | 2/1998 | Rise |
| 5,727,553 A | 3/1998 | Saad |
| 5,755,758 A | 5/1998 | Wolozko |
| 5,776,170 A | 7/1998 | MacDonald et al. |
| 5,792,187 A | 8/1998 | Adams |
| 5,806,522 A | 9/1998 | Katims |
| 5,830,151 A | 11/1998 | Hadzic et al. |
| 5,833,709 A | 11/1998 | Rise |
| 5,853,373 A | 12/1998 | Griffith et al. |
| 5,871,487 A | 2/1999 | Warner et al. |
| 5,893,883 A | 4/1999 | Torgerson |
| 5,895,416 A | 4/1999 | Barreras |
| 5,925,070 A | 7/1999 | King |
| 5,938,690 A | 8/1999 | Law |
| 5,948,007 A | 9/1999 | Starkebaum et al. |
| 5,976,110 A | 11/1999 | Greengrass et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,104,957 A | 8/2000 | Alo et al. |
| 6,159,163 A | 12/2000 | Strauss et al. |
| 6,161,044 A | 12/2000 | Silverstone |
| 6,161,048 A | 12/2000 | Sluijter et al. |
| 6,167,305 A | 12/2000 | Cammilli et al. |
| 6,167,311 A | 12/2000 | Rezai |
| 6,176,242 B1 | 1/2001 | Rise |
| 6,192,278 B1 | 2/2001 | Werner et al. |
| 6,198,963 B1 | 3/2001 | Haim et al. |
| 6,233,488 B1 | 5/2001 | Hess |
| 6,236,892 B1 | 5/2001 | Feler et al. |
| 6,238,423 B1 | 5/2001 | Bardy |
| 6,246,912 B1 | 6/2001 | Sluijter et al. |
| 6,259,952 B1 | 7/2001 | Sluijter et al. |
| 6,314,325 B1 | 11/2001 | Fitz |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,381,496 B1 | 4/2002 | Meadows et al. |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,438,418 B1 | 8/2002 | Swerdlow et al. |
| 6,440,090 B1 | 8/2002 | Schallhorn |
| 6,473,644 B1 | 10/2002 | Terry, Jr. et al. |
| 6,474,341 B1 | 11/2002 | Hunter et al. |
| 6,487,446 B1 | 11/2002 | Hill et al. |
| 6,505,074 B2 | 1/2003 | Boveja et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,724 B2 | 7/2003 | Mann |
| 6,587,727 B2 | 7/2003 | Osorio et al. |
| 6,600,954 B2 | 7/2003 | Cohen et al. |
| 6,609,030 B1 | 8/2003 | Rezai et al. |
| 6,609,031 B1 | 8/2003 | Law et al. |
| 6,610,713 B2 | 8/2003 | Tracey |
| 6,622,047 B2 | 9/2003 | Barrett et al. |
| 6,622,048 B1 | 9/2003 | Mann |
| 6,659,968 B1 | 12/2003 | McClure |
| 6,662,051 B1 | 12/2003 | Eraker et al. |
| 6,671,556 B2 | 12/2003 | Osorio et al. |
| 6,671,557 B1 | 12/2003 | Gliner |
| 6,675,046 B2 | 1/2004 | Holsheimer |
| 6,684,105 B2 | 1/2004 | Cohen et al. |
| 6,687,538 B1 | 2/2004 | Hrdlicka et al. |
| 6,701,190 B2 | 3/2004 | Gliner |
| 6,712,753 B2 | 3/2004 | Manne |
| 6,712,772 B2 | 3/2004 | Cohen et al. |
| 6,714,822 B2 | 3/2004 | King et al. |
| 6,721,603 B2 | 4/2004 | Zabara et al. |
| 6,757,561 B2 | 6/2004 | Rubin et al. |
| 6,795,737 B2 | 9/2004 | Gielen et al. |
| 6,836,685 B1 | 12/2004 | Fitz |
| 6,856,315 B2 | 2/2005 | Eberlein |
| 6,862,480 B2 | 3/2005 | Cohen et al. |
| 6,871,090 B1 | 3/2005 | He et al. |
| 6,871,099 B1 | 3/2005 | Whitehurst et al. |
| 6,875,571 B2 | 4/2005 | Crabtree et al. |
| 6,885,888 B2 | 4/2005 | Rezai |
| 6,892,097 B2 | 5/2005 | Holsheimer et al. |
| 6,895,280 B2 | 5/2005 | Meadows et al. |
| 6,907,293 B2 | 6/2005 | Grill et al. |
| 6,907,295 B2 | 6/2005 | Gross et al. |
| 6,920,357 B2 | 7/2005 | Osorio et al. |
| 6,923,784 B2 | 8/2005 | Stein |
| 6,928,320 B2 | 8/2005 | King |
| 6,941,173 B2 | 9/2005 | Nachum |
| 6,950,707 B2 | 9/2005 | Whitehurst |
| 6,961,618 B2 | 11/2005 | Osorio et al. |

(56) References Cited

U.S. PATENT DOCUMENTS

| | | |
|---|---|---|
| 6,968,237 B2 | 11/2005 | Doan et al. |
| 6,973,346 B2 | 12/2005 | Hafer et al. |
| 6,988,006 B2 | 1/2006 | King et al. |
| 6,990,376 B2 | 1/2006 | Tanagho et al. |
| 7,020,523 B1 | 3/2006 | Lu et al. |
| 7,024,246 B2 | 4/2006 | Acosta et al. |
| 7,024,247 B2 | 4/2006 | Gliner et al. |
| 7,047,079 B2 | 5/2006 | Erickson |
| 7,047,084 B2 | 5/2006 | Erickson et al. |
| 7,054,686 B2 | 5/2006 | MacDonald |
| 7,076,307 B2 | 7/2006 | Boveja et al. |
| 7,082,333 B1 | 7/2006 | Bauhahn et al. |
| 7,117,034 B2 | 10/2006 | Kronberg |
| 7,127,297 B2 | 10/2006 | Law et al. |
| 7,146,224 B2 | 12/2006 | King |
| 7,149,574 B2 | 12/2006 | Yun et al. |
| 7,158,826 B1 | 1/2007 | Kroll et al. |
| 7,162,303 B2 | 1/2007 | Levin et al. |
| 7,162,304 B1 | 1/2007 | Bradley |
| 7,167,750 B2 | 1/2007 | Knudson et al. |
| 7,174,215 B2 | 2/2007 | Bradley |
| 7,177,690 B2 | 2/2007 | Woods |
| 7,177,702 B2 | 2/2007 | Wallace et al. |
| 7,180,760 B2 | 2/2007 | Varrichio et al. |
| 7,206,632 B2 | 4/2007 | King |
| 7,206,640 B1 | 4/2007 | Overstreet |
| 7,206,642 B2 | 4/2007 | Pardo et al. |
| 7,212,865 B2 | 5/2007 | Cory |
| 7,212,867 B2 | 5/2007 | Van Venrooij et al. |
| 7,225,035 B2 | 5/2007 | Brabec et al. |
| 7,228,179 B2 | 6/2007 | Campen et al. |
| 7,231,254 B2 | 6/2007 | DiLorenzo |
| 7,236,822 B2 | 6/2007 | Dobak, III |
| 7,236,830 B2 | 6/2007 | Gliner |
| 7,236,834 B2 | 6/2007 | Christopherson et al. |
| 7,239,912 B2 | 7/2007 | Dobak, III |
| 7,241,283 B2 | 7/2007 | Putz |
| 7,242,984 B2 | 7/2007 | DiLorenzo |
| 7,244,150 B1 | 7/2007 | Brase et al. |
| 7,251,529 B2 | 7/2007 | Greenwood-Van Meerveld |
| 7,252,090 B2 | 8/2007 | Goetz |
| 7,254,445 B2 | 8/2007 | Law et al. |
| 7,260,436 B2 | 8/2007 | Kilgore et al. |
| 7,266,412 B2 | 9/2007 | Stypulkowski |
| 7,276,057 B2 | 10/2007 | Gerber |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,328,068 B2 | 2/2008 | Spinelli et al. |
| 7,329,262 B2 | 2/2008 | Gill |
| 7,333,857 B2 | 2/2008 | Campbell |
| 7,337,005 B2 | 2/2008 | Kim et al. |
| 7,337,006 B2 | 2/2008 | Kim et al. |
| 7,343,200 B2 | 3/2008 | Litvak et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,381,441 B2 | 6/2008 | Leung et al. |
| 7,386,341 B2 | 6/2008 | Hafer et al. |
| 7,389,145 B2 | 6/2008 | Kilgore et al. |
| 7,393,351 B2 | 7/2008 | Woloszko et al. |
| 7,425,142 B1 | 9/2008 | Putz |
| 7,433,734 B2 | 10/2008 | King |
| 7,444,181 B2 | 10/2008 | Shi et al. |
| 7,444,183 B2 | 10/2008 | Knudson et al. |
| 7,444,184 B2 | 10/2008 | Boveja et al. |
| 7,447,546 B2 | 11/2008 | Kim et al. |
| 7,450,993 B2 | 11/2008 | Kim et al. |
| 7,452,335 B2 | 11/2008 | Wells et al. |
| 7,463,927 B1 | 12/2008 | Chaouat |
| 7,483,747 B2 | 1/2009 | Gliner et al. |
| 7,489,969 B2 | 2/2009 | Knudson et al. |
| 7,493,172 B2 | 2/2009 | Whitehurst et al. |
| 7,496,404 B2 | 2/2009 | Meadows et al. |
| 7,502,651 B2 | 3/2009 | Kim et al. |
| 7,502,652 B2 | 3/2009 | Gaunt et al. |
| 7,551,964 B2 | 6/2009 | Dobak, III |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,606,622 B2 | 10/2009 | Reeve |
| 7,610,096 B2 | 10/2009 | McDonald, III |
| 7,613,520 B2 | 11/2009 | De Ridder |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,702,379 B2 | 4/2010 | Avinash et al. |
| 7,711,432 B2 | 5/2010 | Thimineur et al. |
| 7,715,915 B1 | 5/2010 | Rye et al. |
| 7,734,340 B2 | 6/2010 | De Ridder |
| 7,734,352 B2 | 6/2010 | Greenberg et al. |
| 7,734,355 B2 | 6/2010 | Cohen et al. |
| 7,742,810 B2 | 6/2010 | Moffitt et al. |
| 7,761,166 B2 | 7/2010 | Giftakis et al. |
| 7,761,168 B2 | 7/2010 | Gross |
| 7,761,170 B2 | 7/2010 | Kaplan et al. |
| 7,769,463 B2 | 8/2010 | Katsnelson |
| 7,778,704 B2 | 8/2010 | Rezai |
| 7,792,591 B2 | 9/2010 | Rooney et al. |
| 7,801,601 B2 | 9/2010 | Maschino et al. |
| 7,801,604 B2 | 9/2010 | Brockway et al. |
| 7,805,197 B2 | 9/2010 | Bradley |
| 7,809,443 B2 | 10/2010 | Giftakis et al. |
| 7,813,803 B2 | 10/2010 | Heruth et al. |
| 7,813,804 B1 | 10/2010 | Jaax |
| 7,826,901 B2 | 11/2010 | Lee et al. |
| 7,831,306 B2 | 11/2010 | Finch et al. |
| 7,844,338 B2 | 11/2010 | Knudson et al. |
| 7,848,818 B2 | 12/2010 | Barolat et al. |
| 7,853,322 B2 | 12/2010 | Bourget et al. |
| 7,856,277 B1 | 12/2010 | Thacker et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,163 B2 | 2/2011 | Belalcazar |
| 7,890,166 B2 | 2/2011 | Heruth et al. |
| 7,890,176 B2 | 2/2011 | Jaax et al. |
| 7,890,182 B2 | 2/2011 | Parramon et al. |
| 7,890,185 B2 | 2/2011 | Cohen et al. |
| 7,894,907 B2 | 2/2011 | Cowan et al. |
| 7,899,542 B2 | 3/2011 | Cowan et al. |
| 7,914,452 B2 | 3/2011 | Hartley et al. |
| 7,933,654 B2 | 4/2011 | Merfeld et al. |
| 7,937,145 B2 | 5/2011 | Dobak |
| 7,957,797 B2 | 6/2011 | Bourget et al. |
| 7,957,809 B2 | 6/2011 | Bourget et al. |
| 7,979,133 B2 | 7/2011 | Feler et al. |
| 7,996,055 B2 | 8/2011 | Hauck et al. |
| 8,000,794 B2 | 8/2011 | Lozano |
| 8,010,198 B2 | 8/2011 | Libbus et al. |
| 8,016,776 B2 | 9/2011 | Bourget et al. |
| 8,019,423 B2 | 9/2011 | Possover |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,038 B2 | 12/2011 | Simon et al. |
| 8,082,039 B2 | 12/2011 | Kim et al. |
| 8,086,318 B2 | 12/2011 | Strother et al. |
| 8,128,600 B2 | 3/2012 | Gill |
| 8,131,357 B2 | 3/2012 | Bradley et al. |
| 8,150,531 B2 | 4/2012 | Skelton |
| 8,170,658 B2 | 5/2012 | Dacey et al. |
| 8,170,675 B2 | 5/2012 | Alataris et al. |
| 8,180,445 B1 | 5/2012 | Moffitt |
| 8,197,494 B2 | 6/2012 | Jaggi et al. |
| 8,204,607 B2 | 6/2012 | Rooney et al. |
| 8,209,021 B2 | 6/2012 | Alataris et al. |
| 8,209,028 B2 | 6/2012 | Skelton et al. |

(56) References Cited

U.S. PATENT DOCUMENTS

| | | |
|---|---|---|
| 8,214,047 B2 | 7/2012 | Pyles et al. |
| 8,224,453 B2 | 7/2012 | De Ridder |
| 8,224,459 B1 | 7/2012 | Pianca et al. |
| 8,255,048 B2 | 8/2012 | Dal Molin et al. |
| 8,255,057 B2 | 8/2012 | Fang et al. |
| 8,280,515 B2 | 10/2012 | Greenspan |
| 8,301,241 B2 | 10/2012 | Ternes et al. |
| 8,340,775 B1 | 12/2012 | Cullen et al. |
| 8,355,791 B2 | 1/2013 | Moffitt |
| 8,355,792 B2 | 1/2013 | Alataris et al. |
| 8,355,797 B2 | 1/2013 | Caparso |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,380,318 B2 | 2/2013 | Kishawi et al. |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,509,905 B2 | 8/2013 | Alataris et al. |
| 8,509,906 B2 | 8/2013 | Walker et al. |
| 8,554,326 B2 | 10/2013 | Alataris et al. |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,676,331 B2 | 3/2014 | Parker |
| 8,688,212 B2 | 4/2014 | Libbus et al. |
| 8,691,877 B2 | 4/2014 | Yun et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,781 B2 | 5/2014 | Alataris et al. |
| 8,718,782 B2 | 5/2014 | Alataris et al. |
| 8,751,009 B2 | 6/2014 | Wacnik |
| 8,768,469 B2 | 7/2014 | Tweden et al. |
| 8,768,472 B2 | 7/2014 | Fang et al. |
| 8,774,926 B2 | 7/2014 | Alataris et al. |
| 8,805,512 B1 | 8/2014 | Greiner et al. |
| 8,825,164 B2 | 9/2014 | Tweden et al. |
| 8,825,166 B2 | 9/2014 | John |
| 8,874,217 B2 | 10/2014 | Alataris et al. |
| 8,874,221 B2 | 10/2014 | Alataris et al. |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |
| 8,923,964 B2 | 12/2014 | Libbus et al. |
| 8,923,990 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| 9,180,298 B2 | 11/2015 | Alataris et al. |
| 9,205,258 B2 | 12/2015 | Simon et al. |
| 9,211,410 B2 | 12/2015 | Levine et al. |
| 9,220,889 B2 | 12/2015 | Carlton et al. |
| 9,278,215 B2 | 3/2016 | Thacker et al. |
| 9,283,387 B2 | 3/2016 | Thacker et al. |
| 9,283,388 B2 | 3/2016 | Thacker et al. |
| 9,295,840 B1 | 3/2016 | Thacker |
| 9,308,370 B2 | 4/2016 | Lima et al. |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colborn |
| 9,440,074 B2 | 9/2016 | Ternes et al. |
| 9,480,846 B2 | 11/2016 | Strother |
| 9,533,153 B2 | 1/2017 | Libbus et al. |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,700,724 B2 | 7/2017 | Liu et al. |
| 9,724,509 B2 | 8/2017 | Su et al. |
| 9,724,511 B2 | 8/2017 | Wei et al. |
| 9,789,313 B2 | 10/2017 | Lipani |
| 9,833,614 B1 | 12/2017 | Gliner |
| 9,895,532 B2 | 2/2018 | Kaula et al. |
| 9,895,539 B1 | 2/2018 | Heit et al. |
| 9,913,980 B2 | 3/2018 | Ostroff et al. |
| 9,950,173 B2 | 4/2018 | Doan |
| 9,968,732 B2 | 5/2018 | Drew et al. |
| 10,149,978 B1 | 12/2018 | Park |
| 10,188,856 B1 | 1/2019 | Libbus et al. |
| 10,207,109 B2 | 2/2019 | Zhu et al. |
| 10,220,205 B2 | 3/2019 | Bhadra et al. |
| 10,328,264 B2 | 6/2019 | Hamann et al. |
| 10,420,935 B2 | 9/2019 | Illegems |
| 10,485,975 B2 | 11/2019 | Greiner et al. |
| 10,537,740 B2 | 1/2020 | Cabunaru |
| 10,561,845 B2 | 2/2020 | Giftakis et al. |
| 10,632,300 B2 | 4/2020 | Wagenbach et al. |
| 10,675,468 B2 | 6/2020 | Torgerson |
| 10,799,701 B2 | 10/2020 | Lee |
| 10,898,714 B2 | 1/2021 | Libbus et al. |
| 11,045,649 B2 | 6/2021 | Wei et al. |
| 11,058,875 B1 | 7/2021 | Zinner |
| 11,235,153 B2 | 2/2022 | Kibler et al. |
| 2002/0055779 A1 | 5/2002 | Andrews |
| 2002/0087201 A1 | 7/2002 | Firlik et al. |
| 2002/0128700 A1 | 9/2002 | Cross |
| 2002/0198572 A1 | 12/2002 | Weiner |
| 2003/0018368 A1 | 1/2003 | Ansarinia |
| 2003/0100931 A1 | 5/2003 | Mullett |
| 2003/0120323 A1 | 6/2003 | Meadows et al. |
| 2003/0135241 A1 | 7/2003 | Leonard et al. |
| 2003/0135248 A1 | 7/2003 | Stypulkowski |
| 2003/0181958 A1 | 9/2003 | Dobak |
| 2003/0199952 A1 | 10/2003 | Stolz et al. |
| 2003/0204221 A1* | 10/2003 | Rodriguez ......... A61N 1/36071 607/48 |
| 2003/0208244 A1 | 11/2003 | Stein et al. |
| 2003/0212440 A1 | 11/2003 | Boveja |
| 2003/0236558 A1 | 12/2003 | Whitehurst |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 | 6/2004 | Whitehorse |
| 2004/0158119 A1 | 8/2004 | Osorio et al. |
| 2004/0158298 A1 | 8/2004 | Gliner |
| 2004/0158839 A1 | 8/2004 | Gliner et al. |
| 2004/0162590 A1 | 8/2004 | Whitehurst et al. |
| 2004/0167584 A1 | 8/2004 | Carroll et al. |
| 2004/0172085 A1 | 9/2004 | Knudson et al. |
| 2004/0176812 A1 | 9/2004 | Knudson et al. |
| 2004/0186532 A1 | 9/2004 | Tadlock |
| 2004/0186544 A1 | 9/2004 | King |
| 2004/0193228 A1 | 9/2004 | Gerber |
| 2004/0193230 A1 | 9/2004 | Overstreet |
| 2004/0199214 A1 | 10/2004 | Merfeld et al. |
| 2004/0210270 A1 | 10/2004 | Erickson |
| 2004/0210271 A1 | 10/2004 | Campen et al. |
| 2004/0210290 A1 | 10/2004 | Omar-Pasha |
| 2004/0267330 A1 | 12/2004 | Lee et al. |

(56) References Cited

U.S. PATENT DOCUMENTS

| | | |
|---|---|---|
| 2005/0004417 A1 | 1/2005 | Nelson et al. |
| 2005/0004638 A1 | 1/2005 | Cross |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0049664 A1 | 3/2005 | Harris et al. |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0182453 A1 | 8/2005 | Whitehurst et al. |
| 2005/0187591 A1 | 8/2005 | Carter et al. |
| 2005/0222641 A1 | 10/2005 | Pless |
| 2005/0228451 A1 | 10/2005 | Jaax et al. |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0025832 A1 | 2/2006 | O'Keeffe et al. |
| 2006/0030895 A1 | 2/2006 | Simon et al. |
| 2006/0030899 A1 | 2/2006 | O'Keeffe et al. |
| 2006/0041285 A1 | 2/2006 | Johnson |
| 2006/0052836 A1 | 3/2006 | Kim et al. |
| 2006/0069415 A1 | 3/2006 | Cameron et al. |
| 2006/0074450 A1 | 4/2006 | Boveja et al. |
| 2006/0074456 A1 | 4/2006 | Pyles et al. |
| 2006/0079936 A1 | 4/2006 | Boveja et al. |
| 2006/0079937 A1 | 4/2006 | King et al. |
| 2006/0089697 A1 | 4/2006 | Cross et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167498 A1 | 7/2006 | DiLorenzo |
| 2006/0167512 A1 | 7/2006 | Ross et al. |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0206166 A1 | 9/2006 | Weiner |
| 2006/0224187 A1 | 10/2006 | Bradley et al. |
| 2006/0229687 A1 | 10/2006 | Goetz et al. |
| 2006/0253174 A1 | 11/2006 | King |
| 2006/0253182 A1 | 11/2006 | King |
| 2006/0271108 A1 | 11/2006 | Libbus et al. |
| 2007/0021801 A1 | 1/2007 | Heruth et al. |
| 2007/0021803 A1 | 1/2007 | Deem et al. |
| 2007/0025608 A1 | 2/2007 | Armstrong |
| 2007/0027486 A1 | 2/2007 | Armstrong |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0060955 A1 | 3/2007 | Strother et al. |
| 2007/0066995 A1 | 3/2007 | Strother et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0142863 A1 | 6/2007 | Bradley |
| 2007/0142874 A1 | 6/2007 | John |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0156207 A1 | 7/2007 | Kothandaraman et al. |
| 2007/0162088 A1 | 7/2007 | Chen et al. |
| 2007/0167992 A1 | 7/2007 | Carley |
| 2007/0179558 A1 | 8/2007 | Gliner et al. |
| 2007/0179559 A1 | 8/2007 | Giftakis et al. |
| 2007/0179579 A1 | 8/2007 | Feler et al. |
| 2007/0191902 A1 | 8/2007 | Errico |
| 2007/0191906 A1 | 8/2007 | Iyer et al. |
| 2007/0203537 A1 | 8/2007 | Goetz et al. |
| 2007/0208381 A1 | 9/2007 | Hill et al. |
| 2007/0208394 A1 | 9/2007 | King et al. |
| 2007/0213789 A1 | 9/2007 | Nolan et al. |
| 2007/0233194 A1 | 10/2007 | Craig |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0255333 A1 | 11/2007 | Giftakis et al. |
| 2007/0255340 A1 | 11/2007 | Giftakis et al. |
| 2007/0255341 A1 | 11/2007 | Giftakis et al. |
| 2007/0265675 A1 | 11/2007 | Lund |
| 2007/0265681 A1 | 11/2007 | Gerber et al. |
| 2007/0282376 A1 | 12/2007 | Shuros et al. |
| 2007/0293893 A1 | 12/2007 | Stolen et al. |
| 2007/0293915 A1 | 12/2007 | Kilgore et al. |
| 2007/0299482 A1 | 12/2007 | Littlewood et al. |
| 2008/0033511 A1 | 2/2008 | Dobak |
| 2008/0051839 A1 | 2/2008 | Libbus et al. |
| 2008/0058871 A1 | 3/2008 | Libbus et al. |
| 2008/0058878 A1 | 3/2008 | King |
| 2008/0058888 A1 | 3/2008 | King |
| 2008/0065158 A1 | 3/2008 | Ben-Ezra |
| 2008/0086036 A1 | 4/2008 | Hartley |
| 2008/0103570 A1 | 5/2008 | Gerber |
| 2008/0109045 A1 | 5/2008 | Gross et al. |
| 2008/0140153 A1 | 6/2008 | Burdulis |
| 2008/0154329 A1 | 6/2008 | Pyles et al. |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arie et al. |
| 2008/0262411 A1 | 10/2008 | Dobak |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2008/0319514 A1 | 12/2008 | Shi et al. |
| 2009/0018617 A1 | 1/2009 | Skelton et al. |
| 2009/0024186 A1 | 1/2009 | Brockway et al. |
| 2009/0024187 A1 | 1/2009 | Erickson et al. |
| 2009/0036945 A1 | 2/2009 | Chancellor et al. |
| 2009/0048643 A1 | 2/2009 | Erickson |
| 2009/0054950 A1 | 2/2009 | Stephens |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0157183 A1 | 6/2009 | Song |
| 2009/0196472 A1 | 8/2009 | Goetz et al. |
| 2009/0198306 A1 | 8/2009 | Goetz et al. |
| 2009/0204173 A1* | 8/2009 | Fang .................. A61N 1/36071 607/46 |
| 2009/0204192 A1 | 8/2009 | Carlton et al. |
| 2009/0264959 A1 | 10/2009 | Lange |
| 2009/0264973 A1 | 10/2009 | Boling et al. |

(56) References Cited

U.S. PATENT DOCUMENTS

| | | |
|---|---|---|
| 2009/0281595 A1 | 11/2009 | King et al. |
| 2009/0281596 A1 | 11/2009 | King |
| 2009/0287035 A1 | 11/2009 | Dietrich et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0023103 A1 | 1/2010 | Elborno |
| 2010/0036454 A1 | 2/2010 | Bennett et al. |
| 2010/0042170 A1 | 2/2010 | Shuros et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0191307 A1 | 7/2010 | Fang et al. |
| 2010/0228310 A1 | 9/2010 | Shuros et al. |
| 2010/0241190 A1 | 9/2010 | Kilgore et al. |
| 2010/0249876 A1 | 9/2010 | Giftakis et al. |
| 2010/0256696 A1 | 10/2010 | Schleicher et al. |
| 2010/0262205 A1 | 10/2010 | De Ridder |
| 2010/0274312 A1 | 10/2010 | Alataris |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0318157 A1 | 12/2010 | Giftakis et al. |
| 2010/0324630 A1 | 12/2010 | Lee et al. |
| 2010/0331916 A1 | 12/2010 | Parramon et al. |
| 2010/0331920 A1 | 12/2010 | DiGiore et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0040362 A1 | 2/2011 | Godara et al. |
| 2011/0046696 A1 | 2/2011 | Barolat et al. |
| 2011/0071589 A1 | 3/2011 | Starkebaum et al. |
| 2011/0077721 A1 | 3/2011 | Whitehurst et al. |
| 2011/0093042 A1 | 4/2011 | Torgerson et al. |
| 2011/0106208 A1 | 5/2011 | Faltys et al. |
| 2011/0184301 A1 | 7/2011 | Holmstrom et al. |
| 2011/0184486 A1 | 7/2011 | De Ridder |
| 2011/0184488 A1* | 7/2011 | De Ridder ......... A61N 1/36071 607/46 |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2011/0301679 A1 | 12/2011 | Rezai |
| 2012/0010680 A1 | 1/2012 | Wei |
| 2012/0089200 A1 | 4/2012 | Ranu et al. |
| 2012/0150252 A1 | 6/2012 | Feldman et al. |
| 2012/0172946 A1 | 7/2012 | Alataris et al. |
| 2012/0083857 A1 | 8/2012 | Bradley |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0035740 A1 | 2/2013 | Sharma et al. |
| 2013/0041425 A1 | 2/2013 | Fang et al. |
| 2013/0066411 A1 | 3/2013 | Thacker et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110194 A1* | 5/2013 | Wei ................... A61N 1/36071 607/46 |
| 2013/0110196 A1 | 5/2013 | Alataris et al. |
| 2013/0116754 A1 | 5/2013 | Sharma et al. |
| 2013/0123879 A1 | 5/2013 | Alataris et al. |
| 2013/0172955 A1 | 7/2013 | Alataris et al. |
| 2013/0204173 A1 | 8/2013 | Kelly et al. |
| 2013/0204321 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0261695 A1 | 10/2013 | Thacker |
| 2013/0261696 A1 | 10/2013 | Thacker |
| 2013/0282078 A1* | 10/2013 | Wacnik ............... A61N 1/36071 607/59 |
| 2013/0289659 A1 | 10/2013 | Nelson |
| 2014/0031896 A1 | 1/2014 | Alataris et al. |
| 2014/0180361 A1 | 1/2014 | Burdick et al. |
| 2014/0067016 A1 | 3/2014 | Kaula |
| 2014/0081350 A1 | 3/2014 | Zhu |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0276549 A1 | 9/2014 | Osorio |
| 2014/0316484 A1 | 10/2014 | Edgerton |
| 2014/0343622 A1 | 11/2014 | Alataris |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0151125 A1 | 6/2015 | Zhu |
| 2015/0165209 A1 | 6/2015 | Grandhe |
| 2015/0217116 A1 | 8/2015 | Parramon et al. |
| 2015/0321000 A1 | 11/2015 | Rosenbluth |
| 2015/0343220 A1 | 12/2015 | Alataris et al. |
| 2016/0082252 A1 | 3/2016 | Hershey et al. |
| 2016/0114165 A1 | 4/2016 | Levine |
| 2016/0121119 A1 | 5/2016 | Alataris et al. |
| 2016/0158551 A1 | 6/2016 | Kent |
| 2016/0175594 A1 | 6/2016 | Min et al. |
| 2016/0256689 A1 | 9/2016 | Vallejo et al. |
| 2016/0263376 A1 | 9/2016 | Yoo et al. |
| 2016/0271392 A1 | 9/2016 | Vallejo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0036023 A1 | 2/2017 | Parker |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0165485 A1 | 6/2017 | Sullivan et al. |
| 2017/0189686 A1 | 7/2017 | Steinke et al. |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0256906 A1 | 9/2018 | Pivonka |
| 2018/0272132 A1 | 9/2018 | Subbaroyan |
| 2018/0345022 A1 | 12/2018 | Steinke et al. |
| 2019/0022382 A1 | 1/2019 | Gerasimenko et al. |
| 2019/0232064 A1 | 8/2019 | Parker |
| 2019/0321641 A1 | 10/2019 | Baldoni |

(56) References Cited

U.S. PATENT DOCUMENTS

| | | | |
|---|---|---|---|
| 2020/0139138 A1 | 5/2020 | Sit | |
| 2020/0254255 A1 | 8/2020 | Lee | |

FOREIGN PATENT DOCUMENTS

| | | |
|---|---|---|
| EP | 1181947 A2 | 2/2002 |
| EP | 2243510 | 10/2010 |
| EP | 2243511 A2 | 10/2010 |
| EP | 2448633 A1 | 5/2012 |
| EP | 2630984 A1 | 8/2013 |
| EP | 2586491 | 8/2016 |
| GB | 2449546 A | 11/2008 |
| JP | 2002090196 | 3/2002 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2013116368 A1 | 8/2013 |
| WO | WO-2016154091 A1 | 9/2016 |
| WO | WO-2017044904 | 3/2017 |
| WO | WO-2017146658 | 8/2017 |
| WO | WO-2020236946 | 11/2020 |

OTHER PUBLICATIONS

Alo et al., "New Trends in Neuromodulation for the Management of Neuropathic Pain," Neurosurgery, vol. 50, No. 4, Apr. 2002, 15 pages.

Bahdra et al., Stimulation of High-Frequency Sinusoidal Electrical Block of Mammalian Myelinated Axons, J Comput Neurosco, 22:313-326, 2007.

Barolat et al., "Multifactorial Analysis of Epidural Spinal Cord Stimulation," Sterotactic and Functional Neurosurgery, 1991; 56: 77-103.

Bhadra et al., "High Frequency electrical conduction block of the pudendal nerve," Journal of Neural Engineering—Institute of Physics Publishing, 2006, 8 pages.

Bhadra MD, Niloy et al., "High-Frequency Electrical Conduction Block of Mammalian Peripheral Motor Nerve," Muscle and Nerve, Dec. 2005, 9 pages.

Boger et al., "Bladder Voiding by Combined High Frequency Electrical Pudendal Nerve Block and Sacral Root Stimulation," Neurourology and Urodynamics, 27, 2008, 5 pages.

Bowman and McNeal, Response of Single Alpha Motoneurons to High-Frequency Pulse Trains, Appl. Neurophysiol. 49, p. 121-138, 1986, 10 pages.

Burton, Charles, "Dorsal Column Stimulation: Optimization of Application," Surgical Neurology, vol. 4, No. 1, Jul. 1975, 10 pages.

Cuellar et al., "Effect of High Frequency Alternating Current on Spinal Afferent Nociceptive Transmission," Neuromodulation: Technology at the Neural Interface, 2012, 10 pages.

DeRidder et al., "Are Paresthesias necessary for pain suppression in SCS—Burst Stimulation," Brain, Brain Research Center Antwerp of Innovative and Interdisciplinary Neuromodulation, 2010, 27 pages.

DeRidder et al., "Burst Spinal Cord Stimulation: Toward Paresthesia-Free Pain Suppression," www.neurosurgery-online.com, vol. 66, Nos. 5, May 2010, 5 pages.

Grill, Warren et al., "Stimulus Waveforms for Selective Neural Stimulation," IEEE Engineering in Medicine and Biology, Jul./Aug. 1995, pp. 375-385.

Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.

Hopp et al., "Effect of anodal blockade of myelinated fibers on vagal c-fiber afferents," American Journal Physiological Society, Nov. 1980; 239(5), 9 pages.

Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.

Huxely et al., "Excitation and Conduction in Nerve: Quantitative Analysis," Science, Sep. 11, 1964; 145: 1154-9.

Jang et al., "Analysis of Failed Spinal Cord Stimulation Trails in the Treatment of Intractable Chronic Pain," J. Korean Neurosurg Soc 43, 2008, 5 pages.

Kilgore et al. "Nerve Conduction Block Utilizing High-Frequency Alternating Current" Medical & Biology Engineering and Computing, 2004, vol. 24, pp. 394-406.

Kilgore et al. "Reversible Nerve Conduction Block Using Kilohertz Frequency Alternating Current," Neuromodulation Technology at the Neural Interface, International Neuromodulation Society, 2013, 13 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Lachance et al., "Stimulation-induced ectopicity and propagation windows in model damaged axons," J. Comput Neurosci, 2014, 9 pages.

Linderoth et al., "Mechanisms of Spinal Cord Stimulation in Painful Syndromes: Role of Animal Models," Pain Medicine, vol. 7, No. S1, 2006, 13 pages.

Linderoth et al., "Physiology of Spinal Cord Stimulation: Review and Update," Neuromodulation, vol. 2, No. 3, 1999, 15 pages.

Mediati, R.D., , "Mechanisms of Spinal Cord Stimulation," Florence, Oct. 2, 2002, 31 pages.

Melzack, Ronald et al., "Pain Mechanisms: A New Theory," Science, vol. 150, No. 3699, Nov. 19, 1965, 9 pages.

Muller and Hunsperger, "Helvetica Physiologica Acta—Reversible Blockierung der Erregungsleitung im Nerven durch Mittelfrequenz—Daverstrom," Schwabe & Co. Basel, vol. 25, Fasc. 1, 1967, 4 pages.

North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Oakley, John C., "Spinal Cord Stimulation Mechanisms of Action," SPINE vol. 27, No. 22, copyright 2002, 10 pages.

(56) References Cited

OTHER PUBLICATIONS

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.
Simpson, BA, "Spinal Cord Stimulation in 60 cases of Intractable Pain." Journal of Neurology, Neurosurgery and Psychiatry, 1991; 54 pages 196-199.
Simpson, BA, "Spinal Cord Stimulation." British Journal of Neurosurgery, 1997, Feb. 11 (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, Aug. 18, 1962; 195: 712-3.
Tiede et al., "Novel Spinal Cord Stimulation Parameters in Patients with Predominate Back Pain," Neuromodulation: Technology at the Neural Interface, 2013, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Den Honert, Mortimer JT, "A Technique for Collision Block of Peripheral Nerve: Frequency Dependence," MP-11 IEEE Trans. Biomed, Eng. 28: 379-382, 1981.
Wallin et al., "Spinal Cord Stimulation inhibits long-term potentiation of spinal wide dynamic range neurons," Elsevier Science B.V., Brain Research, 5 pages 2003.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhu et al., "Changes in functional properties of A-type but not C-type sensory neurons in vivo in a rat model of peripheral neuropathy," Journal of Pain Research, Dovepress, 2012, 18 pages.
Zhu et al., "Early Demyelination of Primary A-Fibers Induces a Rapid-Onset of Neuropathic Pain in Rat," Neuroscience 200, 2012, 13 pages.
Zhu et al., "Excitability of Aβ sensory neurons is altered in an animal model of peripheral neuropathy," BMC Neuroscience, 13:15, 2012, 15 pages.
"The Need for Mechanism-Based Medicine in Neuromodulation," Neuromodulation: Technology at the Neural Interface, 2012, 7 pages.
Acticare.com website, http://web.archive.org/web/*/acticare.com, Internet Archive Way Back Machine, 2012, 22 pages.
Advanced Neuromodulation Systems, Compustim SCS Systems, Clinical Manual, 1997, 52 pages.
Agnew et al., "Considerations for safety with chronically implanted nerve electrodes," Epilepsia, 31.s2, 1990, 6 pages.
Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural Interface, 2015, 6 pages.
Al-Kaisy et al., Poster: "High-Frequency Spinal Cord Stimulation at 10 kHz for the Treatment of Chronic Back Pain Patients without Prior Back Surgery," 2013, 1 page.
Al-Kaisy., "The use of 10-kilohertz spinal cord stimulation in a cohort of patients with chronic neuropathic limb pain refactory to medical management," Neuromodulation: Technology at the Neural Interface, 18.1, 2015, 6 pages.
Augustinsson et al., "Spinal Cord Stimulation in Cardiovascular Disease," Functional Neurosurgery, vol. 6, No. 1, Jan. 1995, 10 pages.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Stereotactic and Functional Neurosurgery, 1991 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome | [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., Stimulation of High-Frequency Sinusoidal Electrical Block of Mammalian Myelinated Axons, J Comput Neurosco, 22:313-326, 2007.
BionicNAVIGATOR Software Guide, Part MP9055261-001, 2004, 58 pages.
Boston Scientific "Precision™ Spinal Cord Stimulator System Clinician Manual—Directions for Use," Clinician Manual, 2015, 74 pages (pp. I, 9-10).
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Broseta et al., "High-Frequency cervical spinal cord stimulation in spasticity and motor disorders," Advances in Stereotactic and Functional Neurosurgery 7. Springer Viennam 1987, 6 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Suvival During Exposure to Pulsed and Continuous Radiofrequency Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
ClinicalTrials.Gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain,"

(56) References Cited

OTHER PUBLICATIONS

Neuromodulation Technology at the Neural Interface, International Neuromodulation Society, 2014, 8 pages.
De Carolis et al., Poster: "Efficacy of Spinal Cord Stimulation (SCS) in the Treatment of Failed Back Surgery Syndrome (FBSS): a comparative study," 2013, 1 page.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Feeling vs. Function Poster, Mager and Associates Consulting, 2009, 1 page.
Geddes, "A Short History of the electrical stimulation of excitable tissue—Including Electrotherapeutic Applications," The Physiologist, vol. 27, No. 1, Feb. 1984, 51 pages.
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
House et al., "Safety and Efficacy of the House/3M Cochlear Implant in Profoundly Deaf Adults," Otolaryngologic Clinics of North America, vol. 19, No. 2, May 1986, 12 pages.
International Neuromodulation Society 10th World Congress, Neuromodulation: Technology that Improves Patient Care, London, England, May 21-26, 2011, 385 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.
Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2005, 11 pages.
Kilgore et al. "Nerve Conduction Block Utilizing High-Frequency Alternating Current" Medical & Biology Engineering and Computing, 2004, vol. 42, pp. 394-406.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 kHz Spinal Cord Stimulation in Chronic Refactory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016, 12 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.

(56) References Cited

OTHER PUBLICATIONS

Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The MED-EL SONATATI 100 Cochlear Implant: An evaluation of its safety in adults and children," Acta Oto-Laryngologica, vol. 131, No. 5, 2011, 8 pages.
Munglani, Rajesh, "The Longer Term Effect of Pulsed Radiofrequency for Neuropathic Pain," PAIN 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx2016, 3 pages.
Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview www.nevro.com/English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 1 8th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Spinal Cord Stimulation With Interleaved Pulses: A Randomized, Controlled Trial," vol. 10, No. 4, 2007, 9 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley, John C., "Spinal Cord Stimulation in Axial Low Back Pain: Solving the Dilemma," Pain Medicine, vol. 7, No. S1, 2006, 6 pages.
OHSIPP Summer Newsletter, The Official Newsletter for the Ohio Society of Interventional Pain Physicians, vol. 1 Ed. 2, Summer 2010, 8 pages.
Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.
Palmer et al., "Transcutaneous electrical nerve stimulation and transcutaneous spinal electroanalgesia: A preliminary efficacy and mechanisms-based investigation," Physiotherapy, 95, 2009, 7 pages.
Prausnitz et al., "The Effects of Electric Current Applied to Skin: A Review for Transdermal Drug Delivery," Advanced Drug Delivery Reviews 18, 1996, 31 pages.
Precision—Charging System, Advanced Bionic Corporation, Part 9055259-0001, 2005, 2 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Patienet Trial Journal, Advanced Bionic Corporation, Part 9055260-0001, 2004, 10 pages.
Precision Spinal Cord Stimulation—Patient System Handbook, Advanced Bionic Corporation, Part 9055072-0001, 2004, 93 pages.
Precision Spinal Cord Stimulation—Physician Implant Manual, Advanced Bionic Corporation, Part 9055100, 2004, 62 pages.
Precision Spinal Cord Stimulation—Physician Implant Manual, Advanced Bionic Corporation, Part 9055255-0001, 2005, 70 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 pages.
Precision Spinal Cord Stimulation—Remote Control Model SC-5210, Advanced Bionic Corporation, Part 9055257-001, 2005, 2 pages.
Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Pudenz et al., "Development of an Implantable Telestimulator," Proc. 4th Ann. Nat'l Conf. Neuroelectric Soc., Mar. 10-12, 1971, 111-12 ( Wulfsohn, Norman L. and Anthony Sances, Jr. (eds.) 1971, 4 pages.
Pudenz et al., "Neural Stimulation: Clinical and Laboratory Experiences," Surg. Neurol, 39:235-242 (1993).
Rapcan et al., Clinical Study, "High-Frequency—Spinal Cord Stimulation," Indexed and Abstracted in Science Citation Index Expanded and in Journal Citation Reports, 2015, 3 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Remedi Pain Relief—ENM (Electronic Nerve Modulation), https://web.archive.org/web/20050906181041/http://www.remediuk.com/trials.htm, 2005, 5 pages.
Robb et al., "Transcutaneous Electrical Nerve Stimulation vs. Transcutaneous Spinal Electroanalgesia for Chronic Pain Associated with Breast Cancer Treatments," Journal of Pain and Symptom Management, vol. 33, No. 4, Apr. 2007, 10 pages.
Royle, John., "Transcutaneous Spinal Electroanalgesia and Chronic Pain," Physiotherapy, vol. 86, No. 5, May 2000, 1 page.
Schulman et al., "Battery Powered BION FES Network," Proceedings of the 26th Annual Conference of the IEEE EMBS, San Francisco, CA., Sep. 1-5, 2004, 4 pages.
Science Daily, "Chronic Pain Costs U.S. upto $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal Column Electrohypalgesia," Jul. 1969, 8 pages.

(56) References Cited

OTHER PUBLICATIONS

Shelden et al., "Depolarization in the Treatment of Trigeminal Neuralgia," Evaluation of Compression and Electrical Methods Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 4 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.
Simpson, BA, "Spinal Cord Stimulation in 60 cases of Intractable Pain." Journal of Neurology, Neurosurgery and Psychiatry, 1991 54 pp. 196-199.
Sluijter et al., "The Effects of Pulsed Radiofrequency Fields Applied to the Dorsal Root Ganglion—A Preliminary Report," The Pain Clinic, vol. 11, No. 2, 1998, 12 pages.
Smet et al,., "Successful Treatment of Low Back Pain with a Novel Neuromodulation Device," AZ Nikolaas, 2010, 12 pages.
Smet et al., Poster: "High-Frequency Spinal Cord Stimulation at 10 kHz after Failed Traditional Spinal Cord Stimulation," NANS, 2013, 1 page.
St. Jude Medical, "Eon Mini™ Rechargeable IPG, The smallest, longest lasting IPG for enhanced patient satisfaction, "Apr. 29, 2013, 3 pages.
St. Jude Medical, "Individualized Therapy through Diverse Lead Options," 2008, 6 pages.
Stimwave, News Release: Stimwave Receives FDA Approval for High Frequency IDE, http://stimwave.com/newsroom/latest-news, Jun. 9, 2015, 2 pages.
Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Taylor et al., "The Cost Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Tollison et al., "Practical Pain Management Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Van Buyten et al., "Pain Relief for Axial Back Pain Patients," INS Meeting Poster, 2011, 1 page.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," SPINE, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Ward et al., "Variation in Motor Theshold with Frequency Using kHz Frequency Alternating Current," Muscle and Nerve, Oct. 2001, 9 pages.
Webster's Third New International Dictionary of the English Language Unabridge, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Woo MY, Campbell B. "Asynchronous Firing and Block of Peripheral Nerve Conduction by 20KC Alternating Current," Los Angeles Neuro Society, 1964, June 87-94, 5 pages.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Abejon et al., "Is Impedance a Parameter to be Taken into Account in Spinal Cord Stimulation?" Pain Physician, 2007, 8 pages.
Alo et al., "Factors Affecting Impedance of Percutaneous Leads in Spinal Cord Stimulation," International Neuromodulation Society, vol. 9, No. 2, 2006, 8 pages.
Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, Jan. 2018, 9 pages.
Bronstein et al., "The Rationale Driving the Evolution of Deep Brain Stimulation of Constant-Current Devices," International Neuromodulation Society 2014, 5 pages.
McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Nevro—Leadership Through Innovation, J. P. Morgan 36th Annual Healthcare Conference, Jan. 8, 2018, 21 pages.
Renew Neurostimulation System—Clinician's Manual—Advanced Neuromodulation Systems, Life Gets Better, 2000, 77 pages.

(56) References Cited

OTHER PUBLICATIONS

Rosenblueth et al., "The Blocking and Deblocking Effects of Alternating Currents on Nerve," Department of Physiology in Harvard Medical School, Nov. 1938, 13 pages.
St. Jude Medical, "Clinician's Manual—Percutaneous Lead Kit, Models 3143, 3146, 3149, 3153, 3156, 3159, 3183, 3186, 3189," 2016, 24 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
Wesselink et al., Analysis of Current Density and Related Parameters in Spinal Cord Stimulation, IEEE Transaction on Rehabilitation Engineering vol. 6, No. 2, Jun. 1998, 8 pages.
Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.
Cadish, "Stimulation Latency and Comparison of Cycling Regimens in Women Using Sacral Neuromodulation," Feb. 1, 2016, 4 pages.
Ward et al., "Electrical Stimulation Using Kilohertz-Frequency Alternating Current," Journal of the American Physical Therapy Association, vol. 89, No. 2, Feb. 2009, 12 pages.
Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.
Hofmann et al., "Modified Pulse Shapes for Effective Neural Stimulation," Frontiers in Neuroengineering, Sep. 28, 2011, 10 pages.

\* cited by examiner

US 11,590,352 B2

RAMPED THERAPEUTIC SIGNALS FOR MODULATING INHIBITORY INTERNEURONS, AND ASSOCIATED SYSTEMS AND METHODS

CROSS-REFERENCE TO RELATED APPLICATION

The present application claims priority to pending U.S. Provisional Application No. 62/798,334, filed on Jan. 29, 2019, and are incorporated herein by reference.

TECHNICAL FIELD

The present technology is directed generally to ramped therapeutic signals for modulating inhibitory interneurons, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical or paddle leads that include a lead body with a circular or rectangular/triangular/trapezoidal cross-sectional shape and multiple conductive rings or materials spaced apart from each other at the distal end of the lead body. The conductive rings and/or materials operate as individual electrodes or contacts, and the SCS leads are typically implanted either surgically or externally through a needle inserted into the epidural space, often with the assistance of a stylet.

Once implanted, the pulse generator applies electrical pulses to the electrodes, which in turn modify the function of or information transmitted by the patient's nervous system, such as by altering the patient's responsiveness to sensory stimuli and/or altering the patient's motor circuit and/or internal neural circuit output. The electrical pulses can generate sensations that mask or otherwise alter the patient's sensation of pain. For example, in many cases, patients report a tingling or paresthesia that is perceived as more pleasant and/or less uncomfortable than the underlying pain sensation. In other cases, the patients can receive pain relief without paresthesia or other sensations.

DETAILED DESCRIPTION

Figure 1A:
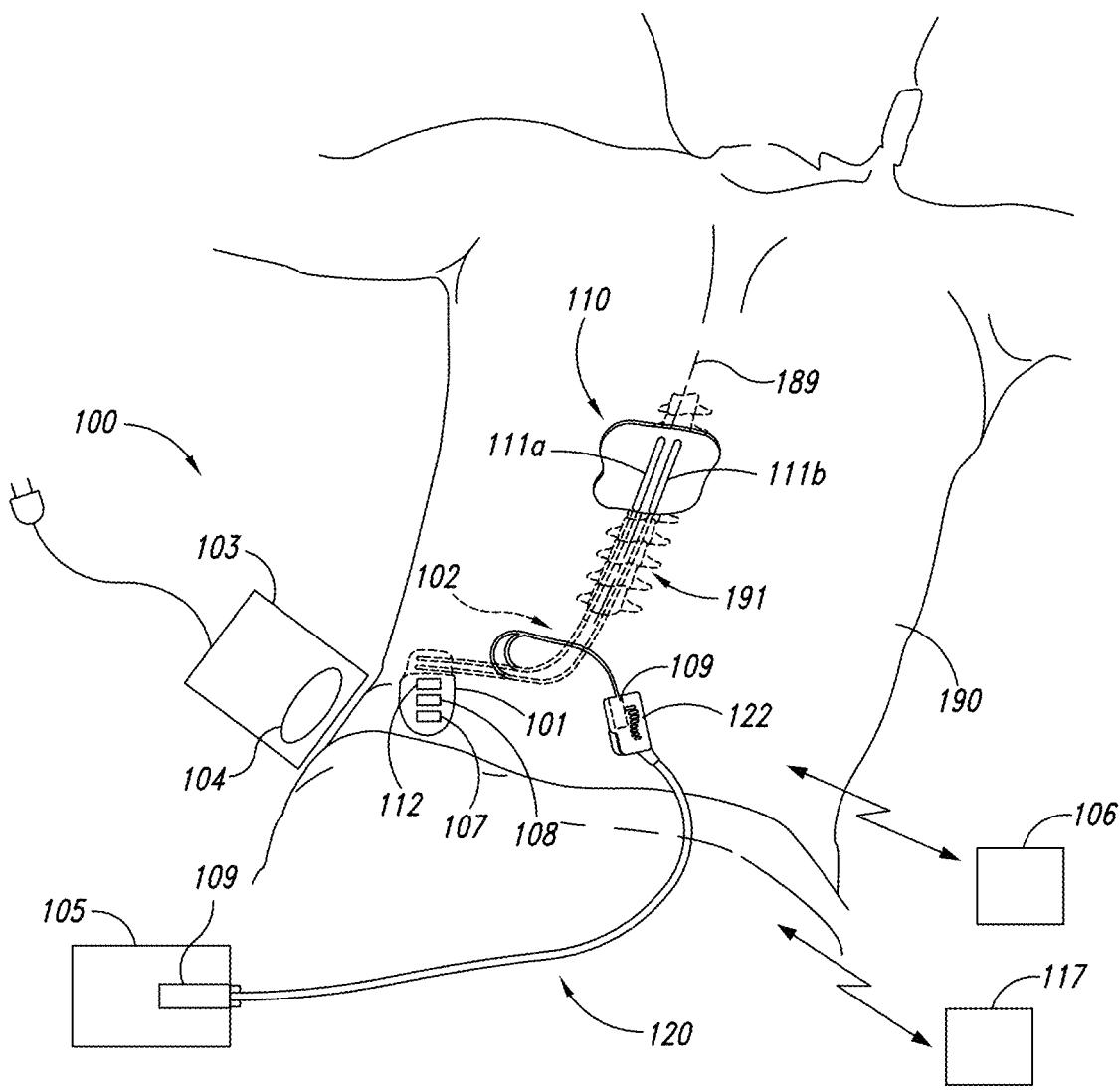
FIG. 1A is a partially schematic illustration of an implantable spinal cord modulation system positioned at a patient's spine to deliver therapeutic signals in accordance with some embodiments of the present technology.

Definitions of selected terms are provided under heading 1.0 ("Definitions"). General aspects of the anatomical and physiological environment in which the disclosed technology operates are described below under heading 2.0 ("Introduction"). Representative treatment systems their characteristics are described under heading 3.0 ("System Characteristics") with reference to FIGS. 1A and 1B. Representative therapeutic signals for activating inhibitory interneurons are described under heading 4.0 ("Representative Therapeutic Signals") with reference to FIGS. 2A-8C. Representative examples are described under heading 5.0 ("Representative Examples").

1.0 Definitions

As used herein, the terms "therapeutic signal," "electrical therapy signal," "electrical signal," "therapeutic electrical stimulation," "therapeutic modulation," "therapeutic modulation signal," and "TS" refer to an electrical signal having (1) a frequency of from about 1 kHz to about 100 kHz, or from about 1.2 kHz to about 100 kHz, or from about 1.5 kHz to about 100 kHz, or from about 2 kHz to about 50 kHz, or from 2 kHz to 25 kHz, or from about 3 kHz to about 20 kHz, or from about 3 kHz to about 15 kHz, or from about 5 kHz to about 15 kHz, or from about 3 kHz to about 10 kHz, or 1 kHz, 2 kHz, 3 kHz, 4 kHz, 5 kHz, 10 kHz, 15 kHz, 20 kHz, 25 kHz, 30 kHz, 40, kHz, 50 kHz, or 100 kHz; (2) an amplitude within an amplitude range of about 0.1 mA to about 20 mA, about 0.5 mA to about 10 mA, about 0.5 mA to about 7 mA, about 0.5 mA to about 5 mA, about 0.5 mA to about 4 mA, about 0.5 mA to about 2.5 mA; (3) a pulse width in a pulse width range of from about 1 microsecond to about 20 microseconds, from about 5 microseconds to about 10 microseconds, from about 1 microseconds to about 500 microseconds, from about 1 microseconds to about 400 microseconds, from about 1 microseconds to about 333 microseconds, from about 1 microseconds to about 166 microseconds, from about 25 microseconds to about 166 microseconds, from about 25 microseconds to about 100 microseconds, from about 30 microseconds to about 100 microseconds, from about 33 microseconds to about 100 microseconds, from about 50 microseconds to about 166 microseconds; and (4) a telemetry window including a 30-microsecond cathodic pulse followed by a 20-microsecond telemetry window followed by a 30-microsecond anodic pulse followed by another 20-microsecond telemetry window, unless otherwise stated, that is delivered for therapeutic purposes.

Unless otherwise stated, the term "about" refers to values within 10% of a stated value.

As used herein, and unless otherwise stated, the TS can be a "first therapeutic signal," and "a second therapeutic signal" refers to a frequency less than 1 kHz.

As used herein, and unless otherwise noted, the terms "modulate," "modulation," "stimulate," and "stimulation" refer generally to signals that have any of the foregoing effects. Accordingly, a spinal cord "stimulator" can have an inhibitory effect on certain neural populations and an excitatory effect on other neural populations.

As used herein, and unless otherwise noted, the term "pulse" refers to a electrical pulse (e.g., a mono-phasic pulse of a bi-phasic pulse pair), and the term "pulse train" refers to a plurality of pulses.

As used herein, and unless otherwise noted, the terms "telemetry window" and "off period" are used interchangeably throughout the application and refer to periods of time where the TS is not being delivered and/or to pauses within the TS itself (e.g., between pulse widths and/or pulse trains). Stimulated neurons can recover from fatigue (e.g., synaptic fatigue) during these telemetry windows and off periods.

The following terms are used interchangeably throughout the present disclosure: "electrical signal," "therapeutic modulation signal," "therapeutic signal," "electrical pulse," "signal," therapeutic signal," "modulation signal," "modulation," "neural modulation signal," and "therapeutic electrical signal."

2.0 Introduction

The present technology is directed generally to treating a patient's condition (e.g., pain) by delivering a therapeutic signal that activates the patient's inhibitory interneurons and associated systems and methods. In some embodiments, the therapeutic signal includes one or more pulses, each pulse having a pulse width. The therapeutic signal can include pulses having pulse widths that are generally similar or different, such as a first pulse width, a second pulse width, a third pulse width, a fourth pulse width, and so on. Each pulse can also have one or more parameters, such as an amplitude, and multiple pulses can define a signal frequency.

In some embodiments, one or more parameters can be increased (e.g, ramped-up) and/or decreased (e.g., ramped-down) from a first value (e.g., the value when the pulse was initiated) to a second value, a third value, etc. during delivery of the pulse. In other embodiments, while the therapeutic signal is being delivered, the increase or decrease occurs from one pulse to the next. For example, the first pulse can be delivered at a first parameter, the second pulse at a second parameter, the third pulse at a third parameter, the fourth pulse at a fourth parameter, and so on. The first parameter can be less than the second parameter, which is less than the third, and so on, or the first parameter can be greater than the second parameter, which is greater than the third, and so on. For example, the first pulse can be delivered at a first amplitude and, during delivery, one or more pulses can be increased to a second amplitude, which is then increased to a third amplitude, to a fourth amplitude, and so on. It is thought that increasing one or more parameters of one or more pulses (e.g., amplitudes) activates inhibitory interneurons to a greater extent than excitatory interneurons. It is also thought that by activating inhibitory interneurons and preventing activation of excitatory interneurons, transmission of a pain signal can be inhibited. Treating a patient's pain using one or more of the ramped therapeutic signals of the present technology can prevent activating excitatory interneurons, and as such, are expected to have an improved outcome compared to therapeutic signals which are not ramped-up, and those which are ramped-down (e.g., for which the first frequency is decreased to a second frequency, and so on).

Specific details of some embodiments of the present technology are described below with reference to representative therapeutic signals to provide a thorough understanding of these embodiments, but some embodiments can have other features. Several details describing structures or processes that are well-known and often associated with delivery of therapeutic signals to treat patient pain, and associated devices, but that may unnecessarily obscure some significant aspects of the disclosure, are not set forth in the following description for purposes of clarity. Moreover, although the following disclosure sets forth some embodiments of different aspects of the technology, some embodiments of the technology can have different configurations, different components, and/or different procedures than those described below. Some embodiments may eliminate particular components and/or procedures. A person of ordinary skill in the relevant art, therefore, will understand that the present technology, which includes associated devices, systems, and procedures, may include some embodiments with additional elements or steps, and/or may include some embodiments without several of the features or steps shown and described below with reference to FIGS. 1A-8C. Several aspects of overall systems in accordance with the disclosed technology are described with reference to FIGS. 1A and 1B, and features specific to leads having sidewall openings are then discussed with reference to FIGS. 2A-8C.

Unless otherwise specified, the specific embodiments discussed are not to be construed as limitations on the scope of the disclosed technology. It will be apparent to one skilled in the art that various equivalents, changes, and modifications may be made without departing from the scope of the disclosed technology, and it is understood that such equivalent embodiments are to be included herein.

It is expected that the techniques described below with reference to FIGS. 1A-8C can produce more effective, more robust, less complicated, and/or otherwise more desirable results than can existing stimulation therapies. In particular, these techniques can produce results that activate inhibitory interneurons as opposed to excitatory interneurons, and/or persist after the modulation signal ceases. These techniques can be performed by delivering modulation signals continuously or intermittently (e.g., on a schedule) to obtain a beneficial effect with respect to treating the patient's pain.

In some embodiments, therapeutic modulation signals are directed to the target location which generally includes the patient's spinal cord, e.g., the dorsal column of the patient's spinal cord. More specifically, the modulation signals can be directed to the dorsal horn, dorsal root, dorsal root ganglion, dorsal root entry zone, and/or other areas at or in close proximity to the spinal cord itself. The foregoing areas are referred to herein collectively as the "spinal cord region." In still further embodiments, the modulation signals may be directed to other neurological structures and/or target neural populations. For example, a device that is used for applying an electrical signal to the spinal cord may be repurposed with or without modifications to administer an electrical signal to another target tissue or organ, e.g., a spinal cord region, or a cortical, sub-cortical, intra-cortical, or peripheral target. As such, any of the herein described systems, subsystems, and/or sub-components serve as means for performing any of the herein described methods.

Without being bound by any of the following theories, or any other theories, it is expected that the therapy signals act to treat the patient's pain and/or other indications via one or both of two mechanisms: (1) by activating at least one of the patient's inhibitory interneurons, and/or (2) by preventing activation of at least one of the patient's excitatory interneurons. The presently disclosed therapy is expected to treat the patient's pain without the side effects generally associated with standard SCS therapies e.g., including but not limited to, paresthesia. Many standard SCS therapies are discussed further in U.S. Pat. No. 8,170,675, incorporated herein by reference. These and other advantages associated with embodiments of the presently disclosed technology are described further below.

3.0 System Characteristics

FIG. 1A schematically illustrates a representative patient therapy system 100 for treating a patient's pain, arranged relative to the general anatomy of the patient's spinal column 191. The system 100 can include a signal generator 101 (e.g., an implanted or implantable pulse generator), which may be implanted subcutaneously within a patient 190 and coupled to one or more signal delivery elements or devices 110. The signal delivery elements or devices 110 may be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms "signal delivery device," "lead," and/or "lead body" include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, which is incorporated herein by reference in its entirety.

In some embodiments, one signal delivery device may be implanted on one side of the spinal cord midline 189, and a second signal delivery device may be implanted on the other side of the spinal cord midline 189. For example, the first and second leads 111a and 111b shown in FIG. 1A may be positioned just off the spinal cord midline 189 (e.g., about 1 mm offset) in opposing lateral directions so that the two leads 111a and 111b are spaced apart from each other by about 2 mm. In some embodiments, the lead or leads 111 may be implanted at a vertebral level ranging from, for example, about T4 to about T12. In some embodiments, one or more signal delivery devices 110 can be implanted at other vertebral levels, e.g., as disclosed in U.S. Pat. No. 9,327,121, which is incorporated herein by reference in its entirety. For example, the one or more signal delivery devices can be implanted using methods and at locations suitable for deep brain stimulation, peripheral nerve stimulation, and/or other types of direct organ stimulation involving implantable leads.

The signal generator 101 can transmit signals (e.g., electrical signals) to the signal delivery elements 110 that excite and/or suppress target nerves (e.g., sympathetic nerves). The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described in the materials incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing as shown in FIG. 1A, or in multiple housings (not shown).

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. For example, the external power source 103 can bypass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the practitioner to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters can be eliminated.

The signal generator 101, the lead extension 102, the trial modulator 105, and/or the connector 122 can each include a receiving element 109. Accordingly, the receiving elements 109 can be patient-implantable elements, or the receiving elements 109 can be integral with an external patient treatment element, device, or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105, and/or the connector 122. The receiving elements 109 can be at least generally similar in structure and function to those described in U.S. Patent Application Publication No. 2011/0071593, which is incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can be updated remotely via a wireless physician programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than the practitioner. For example, the capability of the patient programmer 106 may be limited to starting and/or stopping the signal generator 101 and/or adjusting the signal amplitude. The patient programmer 106 may be configured to accept pain relief input as well as other variables, such as medication use.

In some embodiments, the present technology includes receiving patient feedback, via a sensor, that is indicative of, or otherwise corresponds to, the patient's response to the signal. Feedback includes, but is not limited to, motor, sensory, and verbal feedback. In response to the patient feedback, one or more signal parameters can be adjusted, such as frequency, pulse width, amplitude, or delivery location.

Figure 1B:
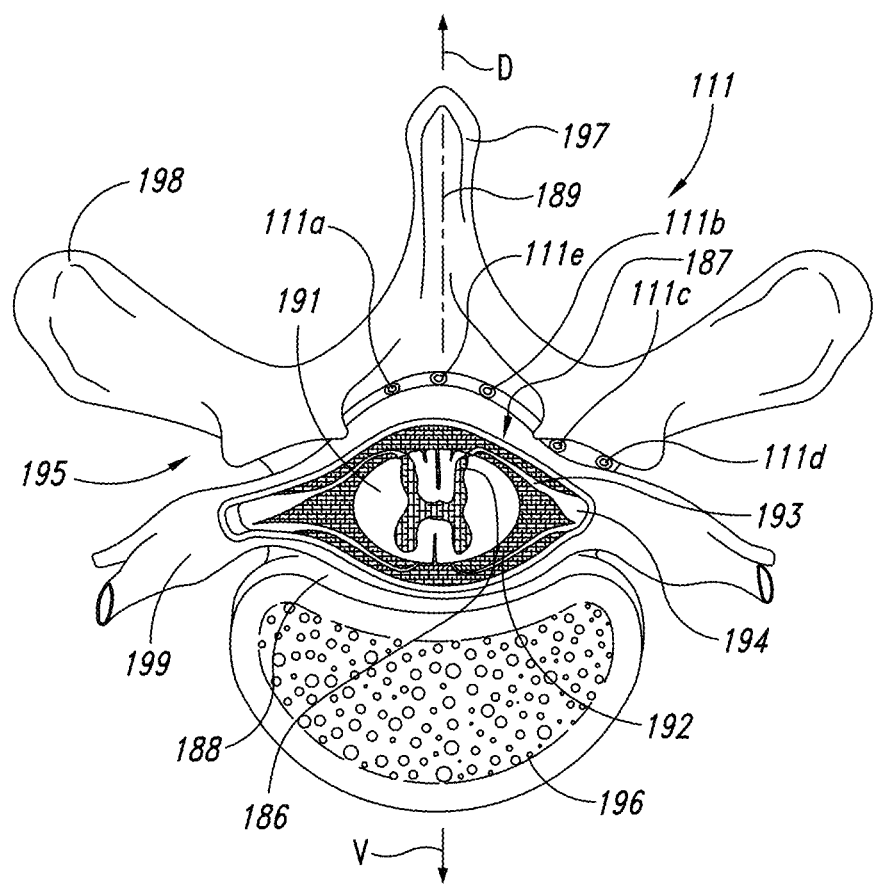
FIG. 1B is a partially schematic, cross-sectional illustration of a patient's spine, illustrating representative locations for implanted lead bodies in accordance with some embodiments of the present technology.

FIG. 1B is a cross-sectional illustration of the spinal cord 191 and an adjacent vertebra 195 (based generally on information from Crossman and Neary, Neuroanatomy, 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated leads; however, the leads 111 can be paddle leads. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry portion 187, and communicate with dorsal horn neurons located at the dorsal horn 186. In some embodiments, the first and second leads 111a and 111b are positioned just off the spinal cord midline 189 (e.g., about 1 mm offset) in opposing lateral directions so that the two leads 111a and 111b are spaced apart from each other by about 2 mm, as discussed above. In some embodiments, a lead or pairs of leads 111 can be positioned at other locations, e.g., toward the outer edge of the dorsal root entry portion 187 as shown by a third lead 111c, or at the dorsal root ganglia 194, as shown by a fourth lead 111d, or approximately at the spinal cord midline 189, as shown by a fifth lead 111e.

Several aspects of the technology are embodied in computing devices, e.g., programmed/programmable pulse generators, controllers, and/or other devices. The computing devices on/in which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In some embodiments, the computer-readable media are tangible media. In some embodiments, the data structures and message structures may be stored or transmitted via an intangible data transmission medium, such as a signal on a communications link. Various suitable communications links may be used, including but not limited to a local area network and/or a wide-area network.

In some embodiments, it is important that the signal delivery device 110 and, in particular, the therapy or electrical contacts of the device, be placed at or proximate to a target location that is expected (e.g., by a practitioner) to produce efficacious results in the patient when the device 110 is activated. Section 4.0 describes ramped therapeutic signals for activating inhibitory interneurons that can be delivered to the patient's spinal cord to treat pain.

4.0 Representative Therapeutic Signals

A. Pertinent Neuronal Physiology and/or Pathophysiology

The following discussion provides further details regarding pertinent physiology and/or pathophysiology for the technology disclosed herein. This section is intended to provide additional context regarding the disclosed technology and the cellular effects associated with neuronal stimulation. The technology disclosed herein is not limited to any particular mechanism of action, and both known and unknown mechanisms of action may be relevant to this technology, including direct effects at the cellular membrane, among others.

Conventional SCS (e.g., SCS at frequencies of 1000 Hz or less, which use paresthesia to mask patient pain), cause direct and indirect effects that ultimately result in pain relief. The direct effects include activation of the subject's dorsal column whereas the indirect effects include propagation of the orthodromic and antidromic action potential (AP), the latter of which results in inhibitory interneuron activation, and ultimately results in inhibition of wide dynamic range (pain-mediating) projection neurons. In addition, antidromic AP propagation may also activate terminal C-fibers, resulting in release of calcitonin gene-related peptide (CGRP).

One possible mechanism of action by which therapeutic signals are expected to treat pain is to reduce the excitability of wide dynamic range (WDR) neurons. It is believed that therapeutic signals can operate in a similar and/or analogous manner as pain treatment to inhibit at least a portion of the patient's sympathetic system. The effect of therapeutic modulation signals on WDR neurons is described in U.S. Pat. No. 9,833,614, previously incorporated by reference herein in its entirety. Specific design requirements and treatment parameters may include determining alternative lead placement within a patient, the type of neuron to target, the frequency of energy delivery, the pulse width, amplitude and combinations thereof, ramping one or more of the frequency of energy delivery, the pulse width, and amplitude up and/or down during delivery of the therapeutic signal, delivery of an alternative number of pulses, and/or prolonging or shortening the length of one or more telemetry windows between one or more pulses of the therapeutic signal.

i. Representative Experiments

Figure 2A:
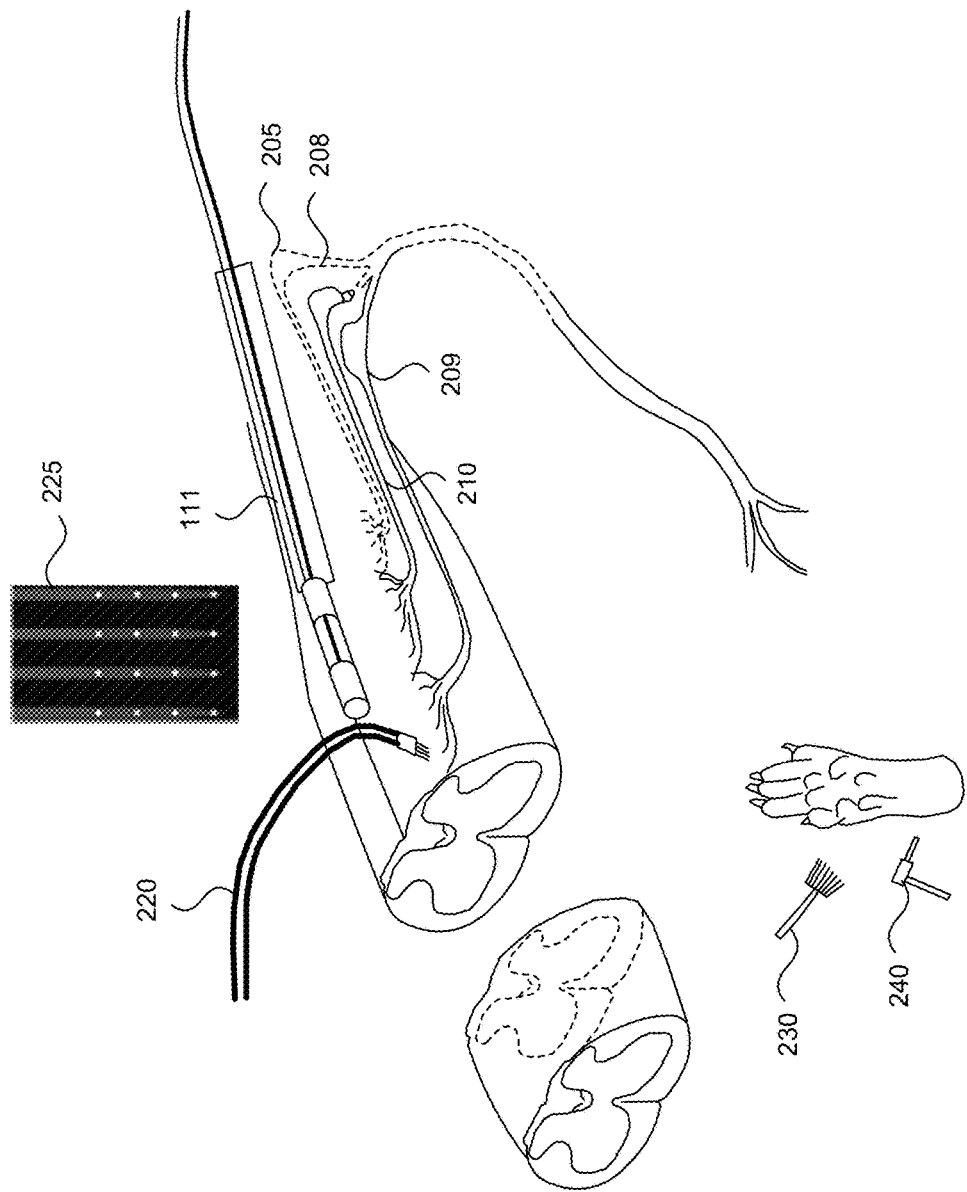
FIG. 2A is a partially schematic illustration of a rat's spinal column illustrating an arrangement for recording neuronal responses to various types of stimulation during therapeutic signal delivery in accordance with some embodiments of the present technology.

FIG. 2A is a partially schematic illustration of a rat's spinal column illustrating an arrangement for recording neuronal responses to various types of stimulation during therapeutic stimulation. Experiments were designed to allow for systematic recording of neural responses from the rat spinal cord following stimulation with either a brush 230 or a Von Frey (VF) pin 240. The therapeutic signal was applied from the lead 111 positioned near the dorsal root entry zone. The lead 111 includes electrodes (not shown) and was placed near the dorsal root and the dorsal lamina II to generate a therapeutic electrical field having a pulse width of about 30 µs and a frequency of 1 kHz to 10 kHz. For illustration purposes, the dorsal root 210 and three lumbar vertebrae (L4 209, L5 208, and L6 205) are shown.

Figure 2B:
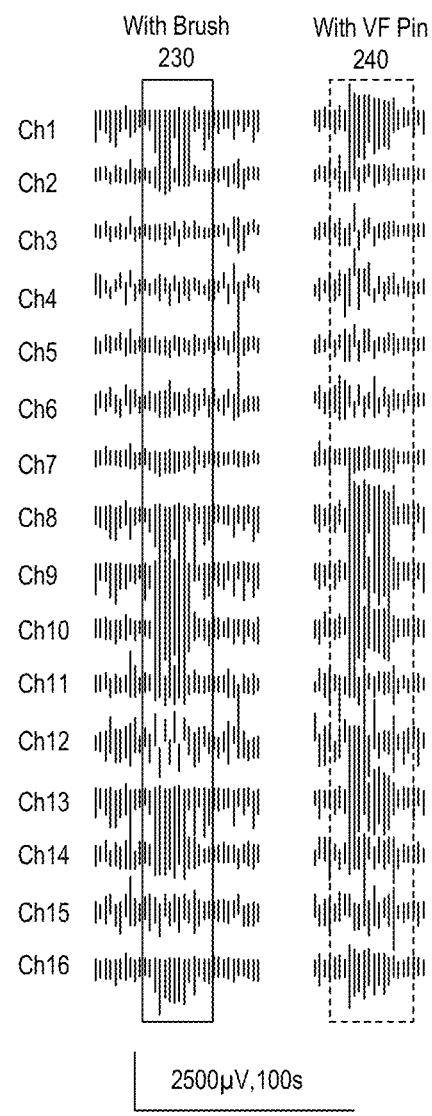
FIG. 2B is a series of charts illustrating certain recordings derived from the arrangement illustrated in FIG. 2A in accordance with some embodiments of the present technology.

A data acquisition system (including Plexon to record extracellular potential and pClamp9 for whole-patch configured to record 40,000 samples per second for extracellular recording(s) and 100,000 samples per second in a whole-patch technique) was used to record the cellular responses to electrical fields having kHz magnitudes. The recording occurred at a target recording site, or more than one target recording site, located within or near the dorsal lamina II. Recordings were performed using a recording setup 220 having 16 distal recording electrodes 225. Cells were identified as single units according the action potential morphology of their firing rates, response to Von Frey (VF) stimulation and relative location of the cell. The data shown in FIG. 2B represent each of the 16 channels. These responses were sorted based on channel and compared between responses to stimulation with a brush 230 and VF pin 240.

Figure 2C:
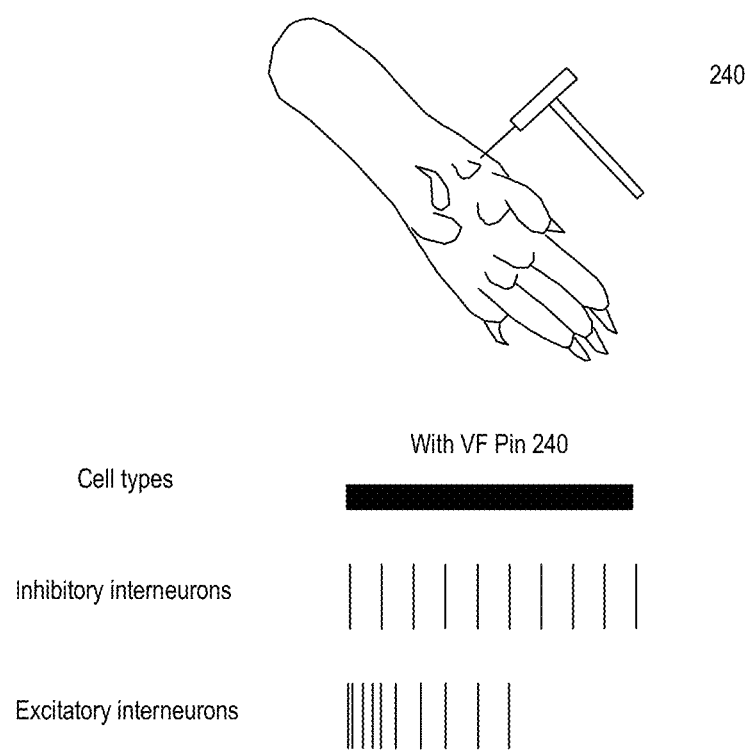
FIG. 2C is a partially schematic illustration of a rat's foot illustrating a stimulation technique and certain neuronal responses thereto in accordance with the present technology.

B. Inhibitory Interneurons and Excitatory Interneurons i. Representative Experimental Data There are at least two different types of interneurons in the dorsal horn of the spinal cord. These include the inhibitory (e.g., non-adapting) interneurons and the excitatory (e.g., adapting) interneurons. As shown in FIG. 2C, the inhibitory interneurons and the excitatory interneurons responded differently to three-zone stimulation via the pin 240. The firing pattern of inhibitory interneurons fired continuously and at a reduced pace compared to excitatory interneurons, which initially fired but ceased.

Figure 3A:
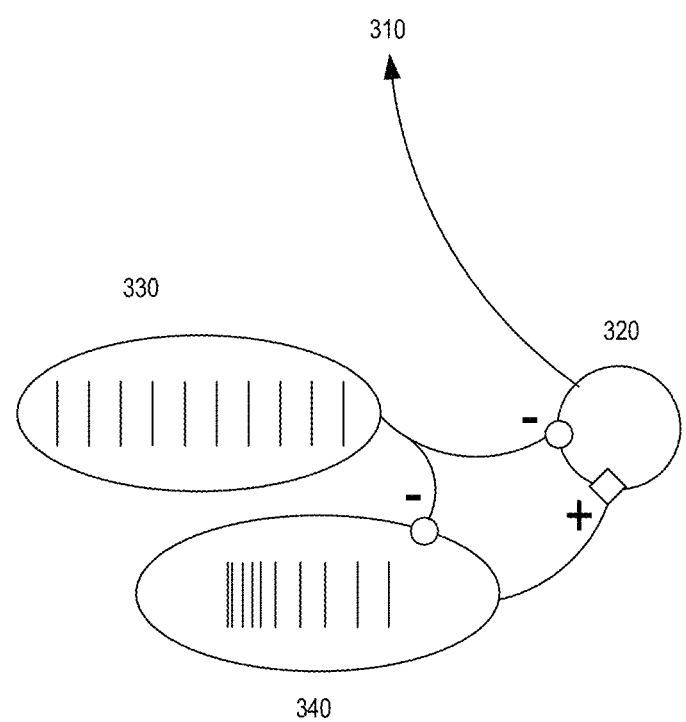
FIG. 3A is a schematic illustration of neural circuits in the patient's spinal cord in accordance with some embodiments of the present technology.

FIG. 3A is a schematic illustration of a neural circuit in the patient's spinal cord. As shown, this neural circuit includes inhibitory neurons 330, excitatory interneurons 340, projection neurons 320, and the brain 310. The projection neurons 320 consolidate the effect of the inhibitory interneurons 330 and the excitatory interneurons 340, and transmit a consolidated output to the brain 310. The firing pattern from FIG. 2C, as an example, is also shown in FIG. 3A, for reference.

Figure 3B:
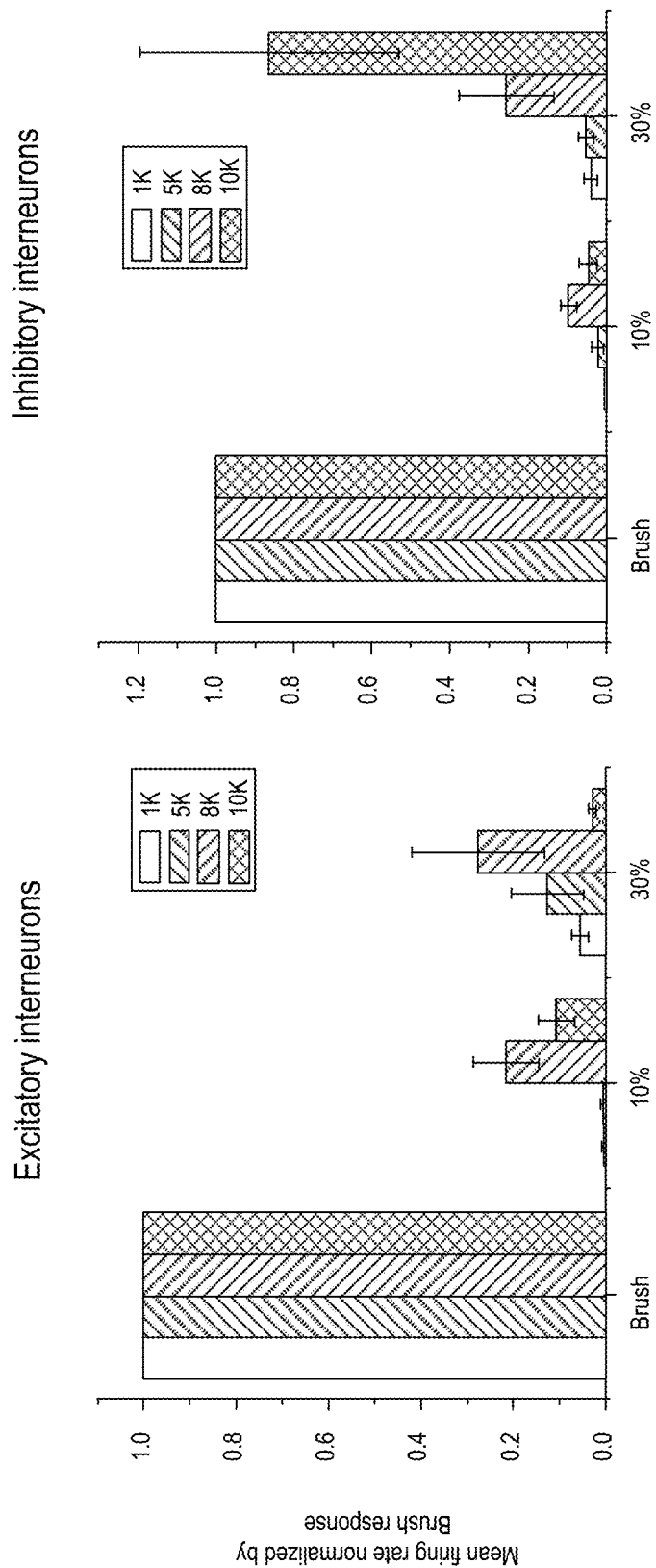
FIG. 3B includes two charts illustrating mean firing rates of excitatory interneurons and inhibitory interneurons in accordance with the present technology.

FIG. 3B includes two charts which illustrate the effect of different frequencies on superficial dorsal horn neurons (e.g., those located in the outer layer, close to the skin surface) at the spinal cord. The effect is shown as the mean firing rates of excitatory interneurons (left) and inhibitory interneurons (right) in response to therapeutic stimulation at four different frequencies (1 kHz, 5 kHz, 8 kHz, and 10 kHz) and at an amplitude of either 10% or 30% of the subject's motor threshold. The mean firing rates were obtained during kHz stimulation and were normalized to the brush response firing rates shown in FIG. 2B. As shown in FIG. 3B, the inhibitory interneurons responded with high mean firing rates in response to a 10 kHz therapeutic signal delivered at 30% of the subject's motor threshold, whereas the excitatory interneurons had a minor response at these stimulation signal parameters. Otherwise, the inhibitory interneurons had lower mean firing rates compared to the excitatory interneurons at all frequencies across both motor thresholds.

Figure 4:
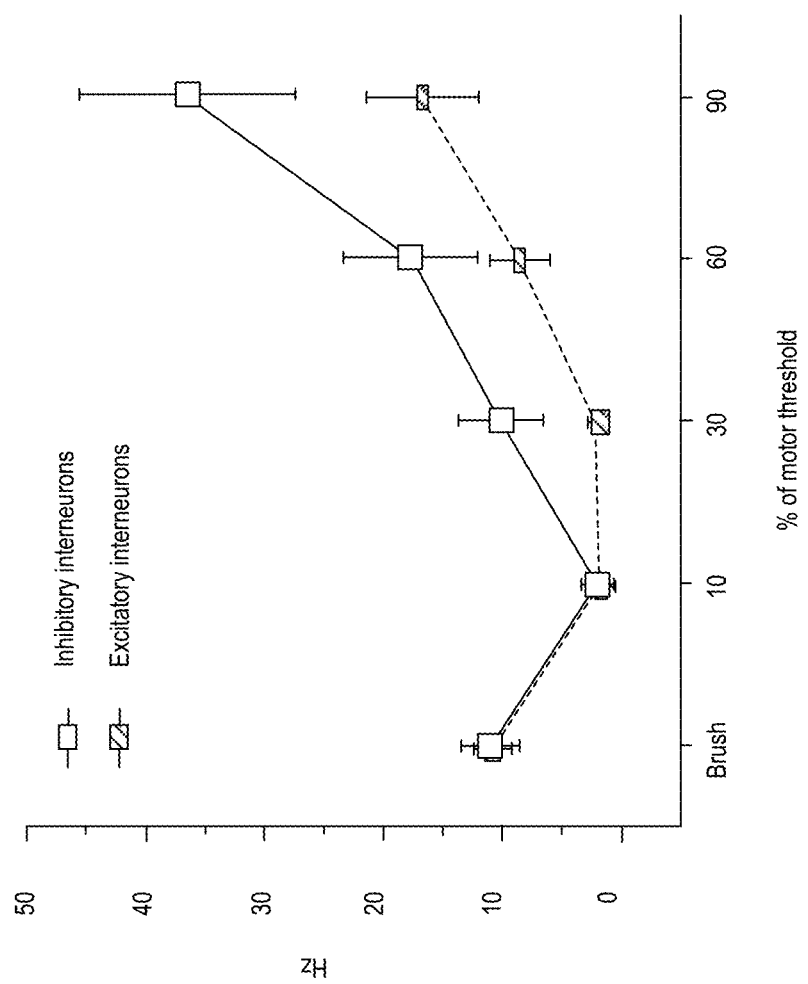
FIG. 4 is a chart illustrating activation of inhibitory interneurons and excitatory interneurons relative to therapeutic signals having various percentages of a patient's motor threshold in accordance with some embodiments of the present technology.

FIG. 4 illustrates activation of inhibitory interneurons and excitatory interneurons in response to a 10 kHz therapeutic signal having various motor threshold levels. The activation levels were computed as firings per second (e.g., Hz, y-axis). In general, interneuron activity increased as the percentage of the subject's motor threshold increased. However, inhibitory interneurons were activated to a greater extent than excitatory interneurons. For example, when the amplitude of the 10 kHz therapeutic signal was at about 10% of the subject's perception threshold, the therapeutic signal did not activate excitatory interneurons or inhibitory interneurons. However, when the amplitude increased to about 30% of the subject's motor threshold, the therapeutic signal activated inhibitory interneurons, but not excitatory interneurons. At 60% of the subject's motor threshold, both excitatory interneurons and inhibitory interneurons increased activities. When the amplitude was increased to 90% of the subject's motor threshold, the inhibitory interneurons were activated to a greater extent than the excitatory interneurons. Clinically, optimal therapeutic outcomes were observed at about 30% of motor threshold (data not shown). Although, in the animal study, higher amplitudes were associated with a larger difference in activation between inhibitory and excitatory neurons (e.g., 60% and 90% of the subject's motor threshold). Without intending to be bound by any particular theory, it is believed that small activations (e.g., more than about 60% of the subject's motor threshold) of excitatory interneurons cancel the pain relief effect provided by activation of inhibitory neurons. Selective activation of inhibitory interneurons at relatively high amplitudes (e.g., greater than about 30% of the subject's motor threshold) without activation of excitatory interneurons may provide significant pain relief.

Figure 5A:
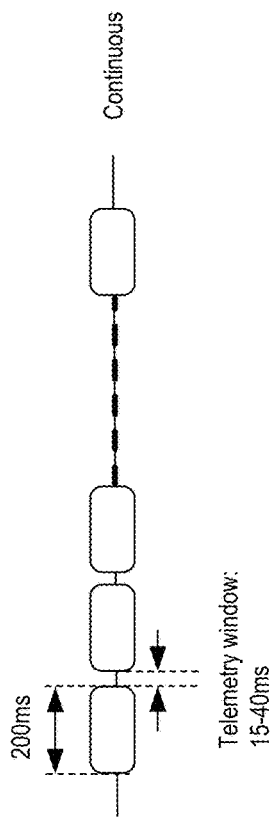
FIG. 5A is an illustration of pulses and telemetry windows in a therapeutic signal in accordance with some embodiments of the present technology.

As shown in FIG. 5A, therapeutic signals of the present technology are not continuous, but rather, include pulse trains, e.g., a series of electrical stimulation signals each followed by a period of no signal delivery. Depending upon the embodiment, the amplitude of individual pulses can be ramped over the time period defined by the pulse width, and/or the ramping can by increasing (or decreasing) the amplitude of one pulse relative to the next pulse. The period of no signal delivery can serve as a telemetry window during which data are exchanged with the signal generator and/or other devices. In the illustrated embodiment, the therapeutic signal of FIG. 5A includes pulse trains having a duration of about 200 milliseconds (ms) followed by a telemetry window of about 15 ms to about 40 ms. In other embodiments, the pulse trains each have a duration of about 500 ms, about 450 ms, about 300 ms, about 250 ms, or about 200 ms.

Figure 5B:
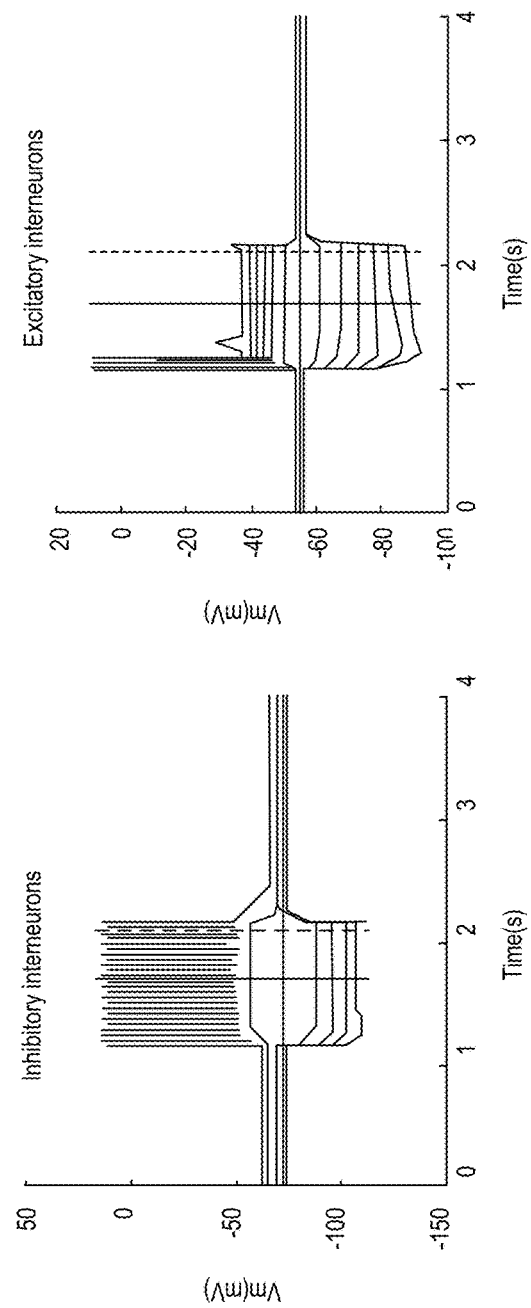
FIG. 5B includes two charts illustrating firing patterns of inhibitory interneurons and excitatory interneurons in response to the therapeutic signal illustrated in FIG. 5A in accordance with some embodiments of the present technology.

FIG. 5B illustrates firing patterns of inhibitory interneurons (left) and excitatory interneurons (right) in response to step pulses at different level(s) of current injections. Without intending to be bound by any particular theory, it is thought that inhibitory interneurons integrate the input signals while excitatory interneurons are sensitive to the difference in the input signals. For example, inhibitory interneurons fire continuously during stimulation, while excitatory interneurons responded with action potentials at the beginning of stimulation.

Without intending to be bound by any particular theory, it is thought that the inhibitory (e.g., non-adapting) interneurons suppress activity of the neural circuit illustrated in FIG. 3A. This neural circuit is thought to increase a patient's pain and as such, activating the inhibitory interneurons may suppress the patient's pain. Similarly, it is thought that, when activated, excitatory interneurons may increase a patient's perception of pain. Accordingly, the therapeutic signals of the present disclosure can have one or more parameters, such as amplitude, that activate an inhibitory interneuron and/or inhibit an excitatory interneuron to treat the patient's pain. For example, it is thought that delivering pulsed therapeutic signals having a ramped amplitude (e.g., an amplitude ramped across a single pulse) affects the response (e.g., firing rates) of interneurons. As shown in FIG. 5B, the inhibitory interneurons (left) fired continuously during delivery of the therapeutic signal (e.g., during delivery of more than one pulse), whereas excitatory neurons fired during an initial portion of a pulse rather than continuously during the therapeutic signal. As such, each pulse of the therapeutic signal activates excitatory interneurons during the initial phase of each pulse (e.g., when the pulse begins).

One approach to reduce activity of the excitatory interneurons is to gradually increase one or more parameters of the therapeutic signal at the beginning of and/or throughout one or more of the pulses, such as ramping one or more of the parameters. It is thought that continuously ramping one or more parameters up during one or more of the pulses (e.g., a ramped stimulation amplitude of the therapeutic signal) can result in greater activation of inhibitory interneurons compared to excitatory interneurons. For example, a ramped therapeutic signal can result in a greater delta (e.g., difference) between activation of inhibitory interneurons and excitatory interneurons.

ii. Representative Ramped Therapeutic Signals

Therapeutic signals of the present technology can be delivered to the target location to treat the patient's pain using one or more motor thresholds. It is thought that increasing the amplitude of the therapeutic signal relative to the patient's motor threshold allows neurons further away from the target location to respond to the therapeutic signal. For example, other SCS therapeutic signals having a frequency in a frequency range of 1 kHz to 100 kHz (or similar SCS therapeutic signals) and which do not generate paresthesia, are delivered up to about 20% of the patient's perception threshold (e.g., about 10% to about 30% of the patient's perception threshold). In some embodiments, the ramped therapeutic signals of the present technology can be delivered at about 10% to about 30% of a patient's perception threshold and using one or more pulse widths having a ramped amplitude.

Figure 6A:
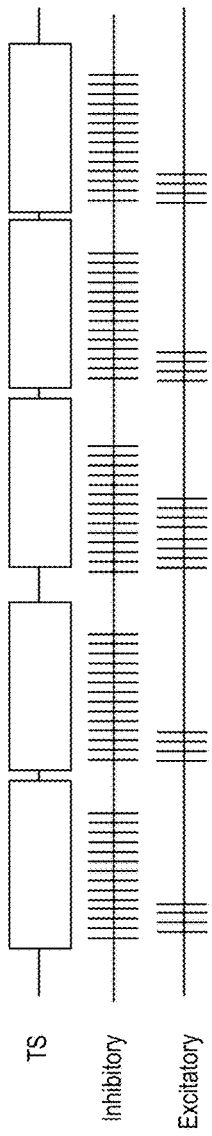
FIG. 6A is an illustration of pulses and telemetry windows in another therapeutic signal, and representative firings of inhibitory interneurons and excitatory interneurons in accordance with some embodiments of the present technology.

FIG. 6A illustrates another representative therapeutic signal of the present technology having a series of pulses (e.g., pulse trains) and telemetry windows (top). The firing rates of inhibitory interneurons (middle) and excitatory interneurons (bottom), which correspond to the illustrated pulse trains, are also shown. In response to a continuous therapeutic signal (e.g., pulse trains having pulses with unramped amplitudes), the inhibitory interneurons fired continuously whereas the excitatory interneurons fired only initially. As such, excitatory interneurons respond to the initial portion of each of the pulse trains and the transition from a telemetry window to the next pulse train may activate the excitatory interneurons.

Figure 6B:
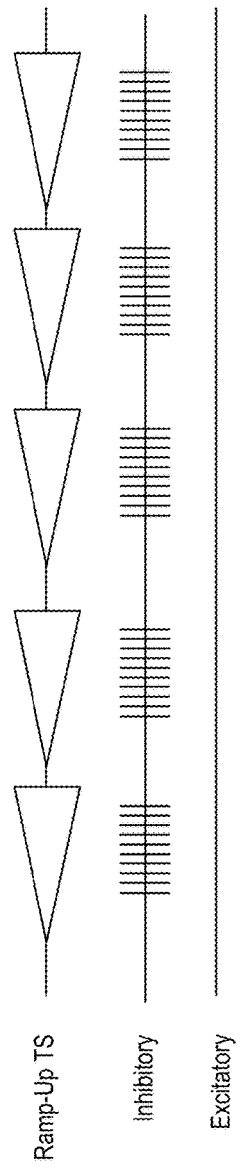
FIG. 6B is an illustration of pulses and telemetry windows in yet another therapeutic signal, and representative firings of inhibitory interneurons and excitatory interneurons in accordance with some embodiments of the present technology.

FIG. 6B illustrates yet another therapeutic signal of the present technology having a series of pulses trains interleaved with telemetry windows (top). In contrast to FIG. 6A, the therapeutic signal of FIG. 6B is a ramped up therapeutic signal and includes pulses having amplitudes that are ramped-up (e.g., increased) over the course of the pulse train. Predicted firing rates of inhibitory interneurons (middle) and excitatory interneurons (bottom), which correspond to the illustrated ramped-up therapeutic signal, are also shown. While it is expected that the inhibitory interneurons will fire continuously in response to the continuous therapeutic signal of FIG. 6A, it is thought that the magnitude of these firing rates may be lower than those of FIG. 6A. In addition, it is thought that ramping therapeutic signals may prevent activation (e.g., firing) of excitatory interneurons. Similar to FIG. 6A, the ramped-up therapeutic signal of FIG. 6B includes telemetry windows and it is thought that ramping up a parameter (e.g., amplitude) of the therapeutic signal during over the course of multiple pulses, may prevent activation of the excitatory interneurons despite the presence of the telemetry window.

Figure 6C:
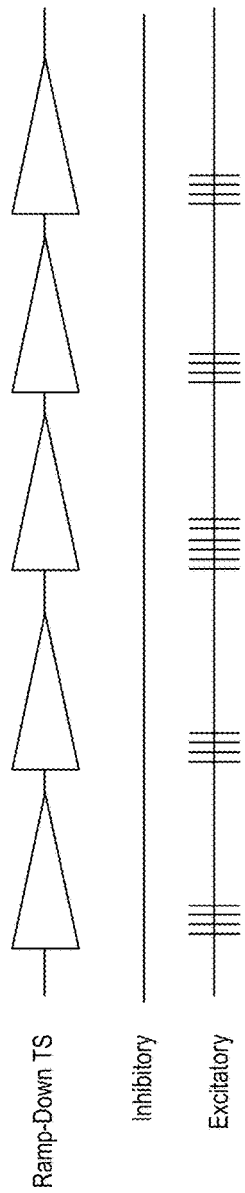
FIG. 6C is an illustration of pulses and telemetry windows in still another therapeutic signal, and representative firings of inhibitory interneurons and excitatory interneurons in accordance with some embodiments of the present technology.

FIG. 6C illustrates still another representative therapeutic signal of the present technology having a series of pulses (pulse trains) and telemetry windows (top). In contrast to FIG. 6B, the signal of FIG. 6C includes pulses having one or more parameters (e.g., amplitude) that are ramped down (e.g., decreased) during delivery of the pulse train. Predicted firing rates of inhibitory interneurons (middle) and excitatory interneurons (bottom), which correspond to the illustrated pulses, are also shown. As illustrated in FIG. 6C, the excitatory interneurons are thought to activate in response to the initial phase of the signal (e.g., where the parameter is at a maximum value relative to the parameter during a remainder of the pulse train) but cease firing as the parameter is ramped down. While not illustrated in FIG. 6C, the inhibitory interneurons may fire at the end or near the end of the pulse train.

The ramped up and ramped down signals were described above with reference to FIGS. 6A-6C as occurring over multiple pulses, e.g. over the course of a pulse train, with individual pulse trains separated by a telemetry window. In other embodiments, the parameter can be varied over the course of a single pulse (e.g., within the duration of a single pulse width), in addition to or in lieu of ramping over the course of multiple pulses. Further examples are provided below with reference to FIGS. 7A-7D FIG. 7A illustrates the ramped-up therapeutic signal 710 of the present technology having a series of pulses with generally similar pulse widths. As shown, the ramped-up therapeutic signal 710 has an amplitude of a first pulse that increases from a first baseline amplitude across a first portion of a first pulse width to a first maximum amplitude. The amplitude of the first pulse then decreases to a first minimum amplitude before returning to the first baseline amplitude. The amplitude of a second pulse increases from a second baseline amplitude across a second portion of a second pulse width to a second maximum amplitude. The amplitude of the second pulse then decreases to a second minimum amplitude before returning to the second baseline amplitude. This pattern can continue with a third pulse width, a fourth pulse width, a fifth pulse width, and so on (not shown).

Figures 7A, 7B, 7C, 7D:
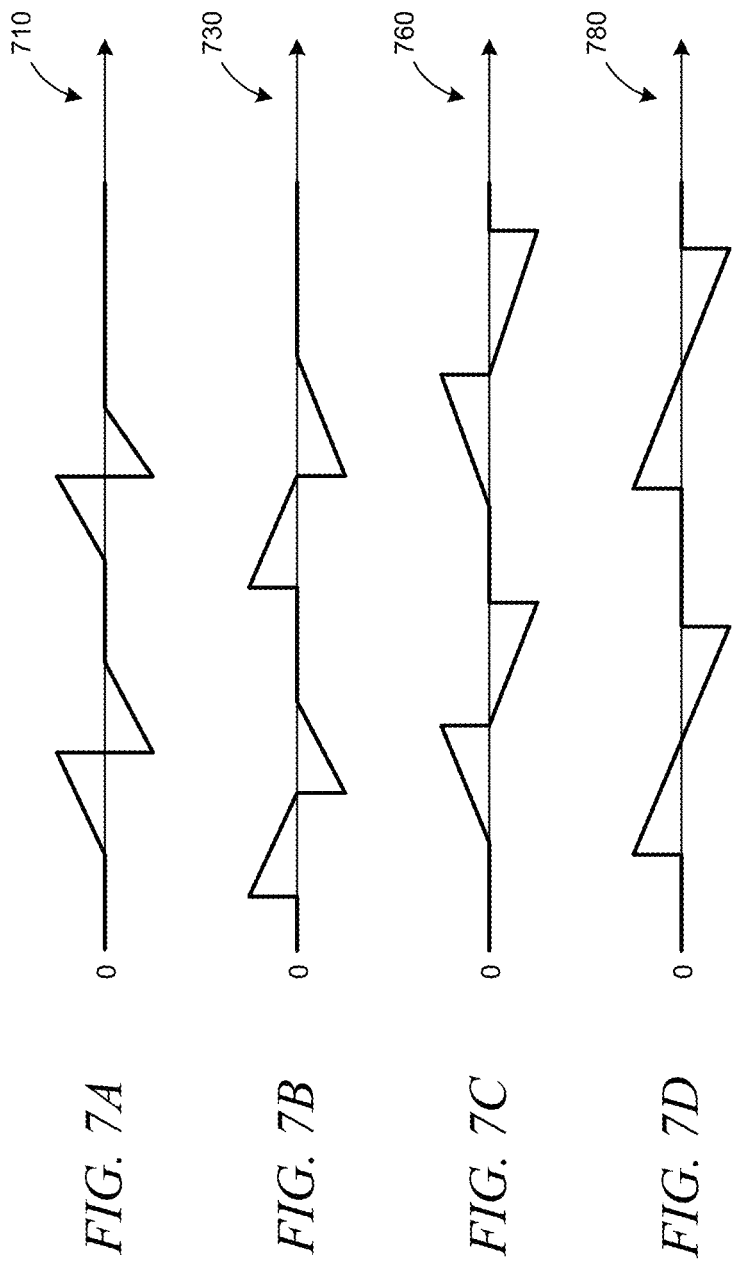
FIG. 7A is an illustration of pulses and telemetry windows in a ramped-up therapeutic signal in accordance with some embodiments of the present technology.
FIG. 7B is an illustration of pulses and telemetry windows a ramped-down therapeutic signal in accordance with some embodiments of the present technology.
FIG. 7C is an illustration of pulses and telemetry windows in a ramped-up and ramped-down therapeutic signal in accordance with some embodiments of the present technology.
FIG. 7D is an illustration of pulses and telemetry windows in a ramped-down and ramped-up therapeutic signal in accordance with some embodiments of the present technology.

FIG. 7B illustrates a ramped-down therapeutic signal 730 of the present technology having a series of pulses. As shown, the ramped-down therapeutic signal 730 has an amplitude of a first pulse that decreases from a first maximum amplitude across a first portion of a first pulse width to a first baseline amplitude. The amplitude of the first pulse then decreases to a first minimum amplitude before returning to the first baseline amplitude. The amplitude of a second pulse decreases from a second maximum amplitude across a second portion of a second pulse width to a second baseline amplitude. The amplitude of the second pulse then decreases to a second minimum amplitude before returning to the second baseline amplitude. This pattern can continue with a third pulse, a fourth pulse, a fifth pulse, and so on (not shown).

FIG. 7C illustrates the ramped-up and ramped-down therapeutic signal of the present technology having a series of pulses. As shown, the ramped-up and ramped-down therapeutic signal 760 has an amplitude of a first pulse that increases from a first baseline amplitude across a first portion of a first pulse width to a first maximum amplitude. The amplitude of the first pulse then decreases to the first baseline amplitude, and further to the first minimum amplitude before returning to the first baseline amplitude. The amplitude of a second pulse increases from a second baseline amplitude across a second portion of a second pulse to a second maximum amplitude. The amplitude of the second pulse then decreases to a second baseline amplitude before decreasing further to a second minimum amplitude before returning to the second baseline amplitude. This pattern can continue with a third pulse, a fourth pulse, a fifth pulse, and so on (not shown).

FIG. 7D illustrates a ramped-down and ramped-up therapeutic signal of the present technology having a series of pulses. As shown, the ramped-down and ramped-up therapeutic signal 780 has an amplitude of a first pulse that begins at a first maximum amplitude during a first portion of a first pulse width and decreases to a first baseline amplitude. The amplitude of the first pulse returns to the first baseline and continues to decrease to the first minimum amplitude before returning to the first baseline amplitude. The amplitude of a second pulse begins at a second maximum amplitude during a second portion of a second pulse width and decreases to a second baseline amplitude. The second pulse continues to decrease to a second minimum amplitude before returning to the second baseline amplitude. This pattern can continue with a third pulse, a fourth pulse, a fifth pulse, and so on (not shown).

Figures 8A, 8B, 8C:
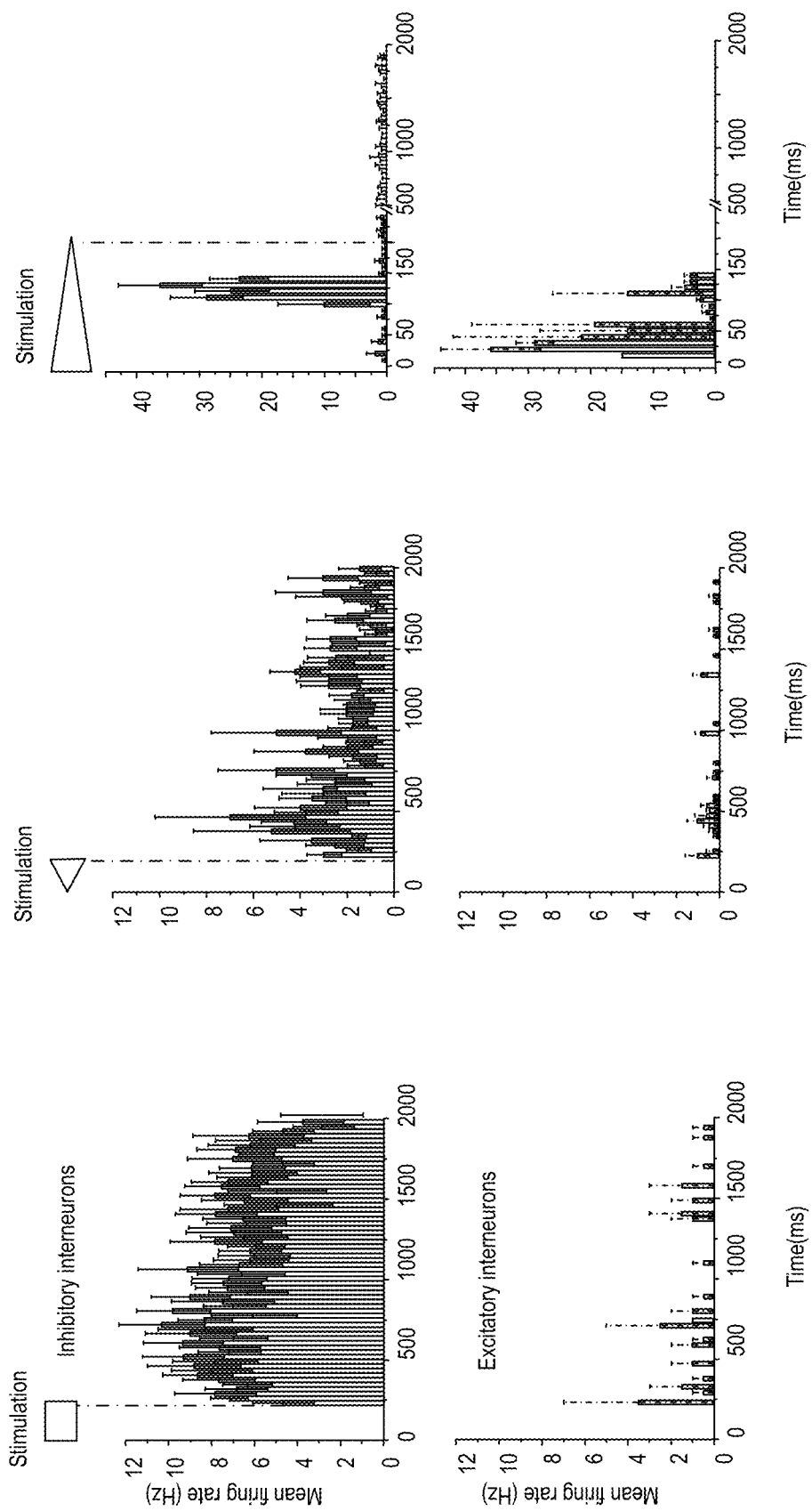
FIG. 8A is a chart illustrating mean firing rates of excitatory interneurons and inhibitory interneurons in response to the therapeutic signal illustrated in FIG. 6A in accordance with embodiments of the present technology.
FIG. 8B is a chart illustrating mean firing rates of excitatory interneurons and inhibitory interneurons in response to the therapeutic signal illustrated in FIG. 6B in accordance with embodiments of the present technology.
FIG. 8C is a chart illustrating mean firing rates of excitatory interneurons and inhibitory interneurons in response to the therapeutic signal illustrated in FIG. 6C in accordance with embodiments of the present technology.

FIG. 8A illustrates mean firing rates of inhibitory interneurons (top) and excitatory interneurons (bottom) in response to the therapeutic signal illustrated in FIG. 6A having pulses with one or more continuous (e.g., non-ramped) parameters (e.g., amplitude) and a 200-millisecond pulse train. As shown, the continuous therapeutic signal activates both inhibitory interneurons and excitatory interneurons; however, the excitatory interneurons are activated to a lesser extent than the inhibitory interneurons. The mean firing rates were computed after discharge (e.g., discharge of the neural impulse from the ganglion cell).

FIG. 8B illustrates mean firing rates of inhibitory interneurons (top) and excitatory interneurons (bottom) in response to the ramped-up therapeutic signal illustrated in FIG. 6B having pulses with one or more ramped-up parameters (e.g., amplitude) and a 200-millisecond pulse train. As shown, the ramped-up therapeutic signal activates inhibitory interneurons to a greater extent than excitatory interneurons. Similar to FIG. 8A, the mean firing rates were computed after discharge. In some embodiments, the ramped-up therapeutic signal of FIG. 8B preferentially activates inhibitory interneurons compared to excitatory interneurons, which may or may not be activated by the ramped-up therapeutic signal. For example, when the ramped-up therapeutic signal activates the excitatory interneurons, it does so to a lesser extent than the inhibitory interneurons. In some embodiments, the ramped-up therapeutic signal is delivered to a patient to treat the patient's pain for a time period extending between minutes and hours per day. In some embodiments, the ramped-up therapeutic signal is delivered to the patient at a first peak amplitude, a second peak amplitude, and a third amplitude throughout the day.

FIG. 8C illustrates mean firing rates of inhibitory interneurons (top) and excitatory interneurons (bottom) in response to the therapeutic signal illustrated in FIG. 6C having pulses with one or more ramped-down parameters (e.g., amplitude) and a 200-millisecond pulse train. As shown, the ramped-down therapeutic signal activates excitatory interneurons to a greater extent and more rapidly than inhibitory interneurons. In addition, the ramped-down therapeutic signal activates excitatory interneurons to a greater extent than the continuous therapeutic signal (e.g., FIGS. 6A and 8A) or ramped-up therapeutic signal (e.g., FIGS. 6B and 8B). However, the excitatory interneurons are largely inactive and not firing once delivery of the ramped-down therapeutic signal has ceased. Unlike the interneurons of FIGS. 8A and 8B, the interneurons of FIG. 8C did not exhibit an after-discharge and, as such, the mean firing rates were computed during stimulation after any stimulation artifacts (e.g., short-duration high-amplitude spikes) had been removed from the data set.

In some embodiments, therapeutic signals in accordance with embodiments of the present technology treat a patient's pain, and associated methods of treating the patient's pain include positioning an implantable signal delivery device proximate to a target location at or near the patient's spinal cord and delivering an electrical therapy signal having at least one parameter (e.g., amplitude) that is increased from a first value to a second value (e.g., ramped) during delivery of one or more pulses. In some embodiments, the parameter is an amplitude of one or more pulses. In some embodiments, the therapeutic signal has a frequency in a frequency range of from 1 kHz to 100 kHz, the amplitude is within an amplitude range of from 0.1 mA to 20 mA, and/or a pulse width within a pulse width range of from 3 microseconds (µs) to 500 µs (e.g., 3 µs to 100 µs).

In some embodiments, ramped therapeutic signals of the present technology include one or more pulse trains, such as a first pulse train and a second pulse train separated from the first pulse train by a telemetry window or a rest period. In some embodiments, the telemetry window has a length of time within a time range of about 15 milliseconds to about 40 milliseconds. In addition, the parameters described herein can be ramped over a pulse train having a time period of from 5 milliseconds to 1000 milliseconds. In some embodiments, the ramped therapeutic signals of the present technology can be delivered to a target location, such as the patient's spinal cord (e.g., along the patient's dorsal column and superior to the patient's sacral region). In some embodiments, the signal delivery device is implanted in the patient's epidural space proximate to the target location.

In some embodiments, the methods described herein include monitoring the patient's pain, and in response to results obtained from monitoring the patient's pain, adjusting at least one signal delivery parameter in accordance with which the electrical signal is applied to the target location.

While embodiments of the present technology may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with pain) can be maintained at pre-treatment levels. For example, the patient can experience a significant reduction in pain largely independent of the patient's movement and/or position. In particular, the patient can assume a variety of positions, consume various amounts of food and liquid, and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to undergo pain treatment (or treatment for corresponding symptoms) while engaging in a variety of activities. This result can also provide an improved lifestyle for patients who experience symptoms associated with pain during sleep.

In some embodiments, patients can choose from a number of signal delivery programs (e.g., two, three, four, five, or six), each with a different amplitude and/or other signal delivery parameter(s), to treat the patient's pain. In some embodiments, the patient activates one program before sleeping and another after waking, or the patient activates one program before sleeping, a second program after waking, and a third program before engaging in particular activities that would trigger, enhance, or otherwise exacerbate the patient's pain. This reduced set of patient options can greatly simplify the patient's ability to easily manage pain, without reducing (and, in fact, increasing) the circumstances under which the therapy effectively addresses the patient's pain. In some embodiments that include multiple programs, the patient's workload can be further reduced by automatically detecting a change in patient circumstance, and automatically identifying and delivering the appropriate therapy regimen. Additional details of such techniques and associated systems are disclosed in U.S. Pat. No. 8,355,797, incorporated herein by reference.

In some embodiments, electrical stimulation may be administered on a pre-determined schedule or on an as-needed basis. Administration may continue for a pre-determined amount of time, or it may continue indefinitely until a specific therapeutic benchmark is reached, e.g., until an acceptable reduction in one or more symptoms is achieved. In some embodiments, electrical stimulation may be administered one or more times per day, one or more times per week, once a week, once a month, or once every several months. Because electrical stimulation is thought to improve the patient's pain over time with repeated use of TS therapy, the patient is expected to need less frequent TS therapy. In some embodiments, the TS therapy can be delivered when the patient's pain recurs or increases in severity. Administration frequency may also change over the course of treatment. For example, a patient may receive less frequent administrations over the course of treatment as certain therapeutic benchmarks are met. The duration of each administration (e.g., the actual time during which a subject is receiving electrical stimulation) may remain constant throughout the course of treatment, or it may vary depending on factors such as patient health, internal pathophysiological measures, or symptom severity. In some embodiments, the duration of each administration may range from 1 to 4 hours, 4 to 12 hours, 12 to 24 hours, 1 day to 4 days, or 4 days or greater.

In some embodiments, therapeutic electrical stimulation to treat a patient's pain is performed with at least a portion of the therapy signal at amplitudes within amplitude ranges of: about 0.1 mA to about 20 mA; about 0.5 mA to about 10 mA; about 0.5 mA to about 7 mA; about 0.5 mA to about 5 mA; about 0.5 mA to about 4 mA; about 0.5 mA to about 2.5 mA; and in some embodiments, surprisingly effective results have been found when treating certain medical conditions with amplitudes below 7 mA.

In some embodiments, therapeutic electrical stimulation to treat a patient's pain is performed with at least a portion of the therapy signal having a pulse width in a pulse width range of from about 1 microseconds to about 500 microseconds; about 1 microsecond to about 400 microseconds; about 1 microsecond to about 333 microseconds; from about 1 microsecond to about 166 microseconds; from about 25 microseconds to about 166 microseconds; from about 25 microseconds to about 100 microseconds; from about 30 microseconds to about 100 microseconds (e.g., less than 100 microseconds); from about 33 microseconds to about 100 microseconds; from about 50 microseconds to about 166 microseconds; and in some embodiments, surprisingly effective results have been found when treating certain medical conditions with pulse widths from about 25 microseconds to about 100 microseconds; and from about 30 microseconds to about 40 microseconds.

In some embodiments, the therapeutic modulation signal may be delivered to a patient having pain at a frequency in a frequency range of 1 kHz to 100 kHz, a pulse width in a pulse width range of 1 microseconds to 333 microseconds, and an amplitude in an amplitude range of 0.1 mA to 20 mA in some embodiments in accordance with the present technology. In addition, the therapy signal can be applied at a duty cycle of 5% to 75%, and can be applied to locations within a patient's spinal cord region to treat the patient's pain.

In some embodiments, therapeutic electrical stimulation to treat a patient's pain is performed with at least a portion of the therapy signal having a telemetry window including a 30-microsecond cathodic pulse followed by a 20-microsecond telemetry window followed by a 30-microsecond anodic pulse followed by another 20-microsecond telemetry window.

Patients can receive multiple signals in accordance with some embodiments, such as two or more signals, each with different signal delivery parameters. For example, the signals can be interleaved with each other, such as 5 kHz pulses interleaved with 10 kHz pulses. In some embodiments, patients can receive sequential "packets" of pulses at different frequencies, with each packet having a duration of less than one second, several seconds, several minutes, or longer depending on the particular patient and indication.

Aspects of the therapy provided to the patient may be varied while still obtaining beneficial results. For example, the location of the lead body (and, in particular, the lead body electrodes or contacts) can be varied throughout and/or across the target location(s) described above, such as target locations proximate to or at various vertebral locations within the patient's spine, and/or other organs, tissues, and/or neurological structures. Other characteristics of the applied signal can also be varied. In some embodiments, the amplitude of the applied signal can be ramped up and/or down and/or the amplitude can be increased or set at an initial level to establish a therapeutic effect, and then reduced to a lower level to save power without forsaking efficacy, as is disclosed in U.S. Patent Publication No. 2009/0204173, which is incorporated herein by reference. The signal amplitude may refer to the electrical current level, e.g., for current-controlled systems, or to the electrical voltage level, e.g., for voltage-controlled systems. The specific values selected for the foregoing parameters may vary from patient to patient and/or from indication to indication and/or on the basis of the selected electrical stimulation location, e.g., the sacral region. The present technology also may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In some embodiments, the parameters in accordance with which the pulse generator provides signals can be modulated during portions of the therapy regimen. For example, the frequency, amplitude, pulse width, pulse train, and/or signal delivery location can be modulated in accordance with a preset program, patient and/or physician inputs, and/or in a random or pseudorandom manner. Such parameter variations can be used to address a number of potential clinical situations, including changes in the patient's perception of one or more symptoms associated with the condition being treated, changes in the preferred target neural population, and/or patient accommodation or habituation.

Electrical stimulation may be applied directly to the spinal cord region, an organ, and/or another target tissue, or it may be applied in close proximity to the spinal cord region, an organ, and/or another target tissue (i.e., close enough to the spinal cord region, the spinal cord region, an organ, and/or another target tissue to receive the electrical signal). For example, electrical stimulation can be applied at or proximate to a target location in the spinal cord region. As another example, the electrical stimulation is applied to other neural tissue such as peripheral nerves corresponding to the spinal cord region (e.g., sympathetic nerves and/or the parasympathetic nerves)

A variety of suitable devices for administering an electrical signal to the spinal cord region, an organ, and/or another target tissue are described in greater detail above in Section 3.0 and may also be described in the references incorporated by reference herein. Examples of devices for administering an electrical signal that can treat pain are disclosed in U.S. Pat. Nos. 8,694,108 and 8,355,797, both of which are incorporated herein by reference in their entireties, and attached as Appendices H and D, respectively. For example, applying electrical stimulation can be carried out using suitable devices and programming modules specifically programmed to carry out any of the methods described herein. For example, the device can comprise a lead, wherein the lead in turn comprises an electrode. In some embodiments, administration of electrical stimulation comprises a positioning step (e.g., placing the lead such that an electrode is in proximity to the spinal cord, sacral region, an organ, and/or another target tissue) and a stimulation step (e.g., transmitting an electrical therapy signal through the electrode). In some embodiments, a device that is used for applying an electrical signal to the spinal cord may be repurposed with or without modifications to administer an electrical signal to another target tissue or organ, e.g., a spinal cord region or a cortical, sub-cortical, intra-cortical, or peripheral target. As such, any of the herein described systems, sub-systems, and/or sub-components serve as means for performing any of the herein described methods.

Many of the embodiments described above are described in the context of treating pain with modulation signals applied to the spinal cord at various vertebral levels. Pain represents an example indication that is expected to be treatable with modulation applied at this location. In some embodiments, modulation signals having parameters (e.g., frequency, pulse width, amplitude, and/or duty cycle) generally similar to those described above can be applied to other patient locations to address other indications, such as those having corresponding abnormal neural system activity (e.g., epilepsy, Parkinson's disease, mood disorders, obesity, and dystonia).

The methods disclosed herein include and encompass, in addition to methods of making and using the disclosed devices and systems, methods of instructing others to make and use the disclosed devices and systems. For example, a method in accordance with some embodiments includes treating a patient's pain by applying a therapeutic signal to the patient's spinal cord region, with the electrical signal being one or more pulse trains, each pulse train having a pulse train duration range from about 3 milliseconds to about 5 seconds and having more than one pulse width. A duration of one or more pulse widths within the pulse train can differ from a duration of one or more other pulse widths within the same pulse train. For example, a first pulse width can be longer or shorter than a second pulse width which can be longer or shorter than a third pulse width, and so on. Likewise, the first pulse width can be associated with a first frequency that differs from a second frequency associated with the second pulse width and/or a third frequency associated with the third pulse width. The electrical signal has a frequency in a range of from about 1 kHz to about 100 kHz, a pulse width in a pulse width range of 1 microseconds to 333 microseconds across a single phase or a single bi-phasic set of pulses, an amplitude in an amplitude range of 0.1 mA to 20 mA, and/or a duty cycle of 1% to 99%, where at least one of these parameters of the electrical signal is ramped up at least during one of the pulse widths, such as amplitude.

A method in accordance with another embodiment includes programming a device and/or system to deliver such a method, instructing or directing such a method. Accordingly, any and all methods of use and manufacture disclosed herein also fully disclose and enable corresponding methods of instructing such methods of use and manufacture.

From the foregoing, it will be appreciated that some embodiments of the present technology have been described herein for purposes of illustration, but that various modifications may be made without deviating from the technology. As described above, signals having the foregoing characteristics are expected to provide therapeutic benefits for patients having pain when stimulation is applied at the patient's spinal cord region. In some embodiments, the present technology can be used to address one or more pain indications, such as those described in the references incorporated by reference, besides and/or in addition to those described herein.

In any of the foregoing embodiments, aspects of the therapy provided to the patient may be varied within or outside the parameters used during the experimental testing and computational models described above, while still obtaining beneficial results for patients suffering neurogenic and/or other disorders. For example, the location of the lead body (and, in particular, the lead body electrodes) can be varied over the significant lateral and/or axial ranges described above. Other characteristics of the applied signal can also be varied and or ramped in a manner different than those described herein. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In some embodiments, the duty cycle may be varied from the ranges of values described above, as can the lengths of the on/off periods. For example, it has been observed that patients can have therapeutic effects (e.g., pain reduction) that persist for significant periods after the stimulation has been halted. In some embodiments, the beneficial effects can persist for 10 to 20 minutes in some cases, and up to several hours or even days in others. Accordingly, the simulator can be programmed to halt stimulation for periods of up to several hours, with appropriate allowances for the time necessary to re-start the beneficial effects. This arrangement can significantly reduce system power consumption, compared to systems with higher-duty cycles, and compared to systems that have shorter on/off periods.

In any of the foregoing embodiments, the parameters in accordance with which the signal generator 102 in FIG. 1A provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Some embodiments of the foregoing systems and methods may be simplified or eliminated in some embodiments of the present disclosure.

Some embodiments of the disclosure described in the context of some embodiments may be combined or eliminated in other embodiments. For example, as described above, the trial period, operating room mapping process, and/or external stimulator may be eliminated or simplified in some embodiments. Therapies directed to some indications may be combined in still further embodiments. Further, while advantages associated with some embodiments have been described in the context of those embodiments, other embodiments may also exhibit such advantages, and not all embodiments need necessarily exhibit such advantages to fall within the scope of the present disclosure. The following examples provide additional embodiments of the disclosure.

Several of the embodiments described above include modifying cell membrane potentials to achieve a therapeutic result. The result can be identified on a larger scale by observing and/or recording a change in the patient's condition (e.g., a reduction in symptoms resulting from the target indication). The result can be identified on a smaller scale by conducting tissue-level and/or cellular-level testing. Representative techniques include electrophysiological and/or electromyographical testing to demonstrate changes in the activation threshold of some cells and/or groups of cells.

To the extent the foregoing materials and/or any other materials incorporated herein by reference conflict with the present disclosure, the present disclosure controls.

The invention claimed is:

1. A method for treating a patient's pain, comprising delivering an electrical therapy signal to a target location via a signal delivery device; wherein
the electrical therapy signal has multiple pulses at a frequency in a frequency range of from 1.2 kHz to 100 kHz,
an amplitude of an individual pulse of the multiple pulses is ramped in only a single direction from a first value to a second value over the individual pulse's duration,
the individual pulse is at a single polarity over the individual pulse's duration, and
the electrical therapy signal preferentially activates inhibitory interneurons.

2. The method of claim 1 wherein the amplitude is within an amplitude range of from 2 mA to 20 mA.

3. The method of claim 2 wherein the amplitude is ramped across more than one individual pulse.

4. The method of claim 1 wherein the target location includes a target nerve fiber.

5. The method of claim 4 wherein the target location is in the patient's spinal cord.

6. The method of claim 5 wherein the target location is along the patient's dorsal column and superior to the patient's sacral region.

7. The method of claim 1 wherein the electrical therapy signal treats the patient's pain without relying on paresthesia or tingling to mask the patient's sensation of the pain.

8. The method of claim 1 wherein the multiple pulses are configured in a first pulse train and a second pulse train separated from the first pulse by a telemetry window.

9. The method of claim 8 wherein the first pulse train and/or the second pulse train have a duration of from about 3 microseconds to about 5 seconds.

10. The method of claim 1 wherein the amplitude is increased over a period of from one microsecond to 333 microseconds.

11. The method of claim 10 wherein the amplitude is increased over a period of less than 100 microseconds.

12. The method of claim 11 wherein the amplitude is increased over a period of from 1 microsecond to 400 microseconds.

13. The method of claim 1, further comprising
positioning the signal delivery device proximate to the target location at or near the patient's spinal cord.

14. The method of claim 13 wherein the signal delivery device is implanted in the patient's epidural space proximate to the target location.

15. The method of claim 1, further comprising:
monitoring the patient's pain; and
in response to results obtained from monitoring the patient's pain;
adjusting at least one signal delivery parameter in accordance with which the electrical signal is applied to the target location, or
terminating delivery of the electrical therapy signal.

16. A method for alleviating a patient's pain, comprising:
programming a signal generator to generate and deliver an electrical therapy signal to a target location, via at least one implanted electrode electrically coupled to the signal generator, to alleviate the patient's pain; wherein
the electrical therapy signal has multiple pulses at a frequency in a frequency range of from 1.2 kHz to 100 kHz,
the signal generator is programmed to ramp an amplitude of an individual pulse of the multiple pulses in only a single direction from a first value to a second value over the individual pulse's duration, the individual pulse being at a single polarity over the individual pulse's duration, and
the electrical therapy signal preferentially activates inhibitory interneurons.

17. The method of claim 16 wherein the signal generator is programmed to ramp the amplitude over a time period of from 1 microsecond to 400 microseconds.

18. The method of claim 16, wherein the amplitude is between 2 mA and 20 mA.

19. The method of claim 16 wherein the electrical therapy signal alleviates the patient's pain without relying on paresthesia or tingling to mask the patient's sensation of the pain.

20. The method of claim 16 wherein the signal delivery device is implanted in the patient's epidural space proximate to the target location.

21. A system for alleviating a patient's pain, comprising:
a signal delivery device carrying at least one electrode, the at least one electrode being positionable at or near a target location within the patient; and
a signal generator coupleable to the at least one electrode and programmed to:
generate an electrical therapy signal having multiple pulses at a frequency in a frequency range of from 1.2 kHz to 100 kHz,
ramp an amplitude of an individual pulse of the multiple pulses in only a single direction from a first value to a second value over the individual pulse's duration, wherein the individual pulse is at a single polarity over the individual pulse's duration, and
deliver the electrical therapy signal having the ramped amplitude to the target location via the at least one electrode to preferentially activate inhibitory interneurons and alleviate the patient's pain.

22. The system of claim 21 wherein the signal generator is programmed to ramp the amplitude over a time period in a range of from about 1 microsecond to about 400 microseconds.

23. The system of claim 21 wherein the electrode is implantable.

24. The system of claim 21 wherein the electrical therapy signal remains on for a period of at least a few milliseconds at a time.

25. A method for treating a patient's pain, comprising:
programming a signal delivery device to deliver an electrical therapy signal to a target location, wherein
the electrical therapy signal includes multiple pulses at a frequency in a frequency range of from 1.2 kHz to 100 kHz,
an amplitude of an individual pulse of the multiple pulses is ramped in only a single direction from a first value to a second value over the individual pulse's duration, and
the individual pulse is at a single polarity over the individual pulse's duration.

* * * * *